US009177677B2

(12) United States Patent
Kurosawa et al.

(10) Patent No.: US 9,177,677 B2
(45) Date of Patent: Nov. 3, 2015

(54) UNDERWATER REMOTE INSPECTION DEVICE AND METHOD FOR UNDERWATER REMOTE INSPECTION

(75) Inventors: Koichi Kurosawa, Hitachi (JP); Satoru Aoike, Tokai (JP); Shinya Ohmori, Mito (JP); Junya Kaneda, Hitachi (JP)

(73) Assignee: HITACHI-GE NUCLEAR ENERGY, LTD., Ibaraki (JP)

(*) Notice: Subject to any disclaimer, the term of this patent is extended or adjusted under 35 U.S.C. 154(b) by 920 days.

(21) Appl. No.: 12/907,161

(22) Filed: Oct. 19, 2010

(65) Prior Publication Data
US 2011/0091002 A1 Apr. 21, 2011

(30) Foreign Application Priority Data

Oct. 20, 2009 (JP) ................................. 2009-241370

(51) Int. Cl.
G21C 17/01 (2006.01)
G21C 17/013 (2006.01)
G21C 17/003 (2006.01)
G01N 1/32 (2006.01)
G21C 19/20 (2006.01)

(52) U.S. Cl.
CPC ............... *G21C 17/003* (2013.01); *G01N 1/32* (2013.01); *G21C 17/013* (2013.01); *G21C 19/207* (2013.01)

(58) Field of Classification Search
USPC .................................................. 376/249, 305
See application file for complete search history.

(56) References Cited

U.S. PATENT DOCUMENTS

| 4,691,724 | A | * | 9/1987 | Garcia et al. ............... 134/169 R |
| 6,636,579 | B2 | * | 10/2003 | Kurosawa et al. ............ 376/305 |
| 7,368,016 | B2 | | 5/2008 | Katsuoka et al. |
| 2010/0089164 | A1 | * | 4/2010 | Aoike et al. .................... 73/632 |

FOREIGN PATENT DOCUMENTS

| JP | 07-198888 A | 8/1995 |
| JP | 9-89786 A | 4/1997 |
| JP | 3890239 B2 * | 3/2002 |
| JP | 2002-257697 A | 9/2002 |
| JP | 2002-340757 A | 11/2002 |
| JP | 2003-255074 A | 9/2003 |
| JP | 2003-262695 A | 9/2003 |
| JP | 2003-337192 A | 11/2003 |
| JP | 2004-325246 A | 11/2004 |
| JP | 3890239 B2 | 12/2006 |
| JP | 2010-96563 A | 4/2010 |
| WO | 2005-105322 A1 | 11/2005 |

* cited by examiner

*Primary Examiner* — Jack W Keith
*Assistant Examiner* — Sean P Burke
(74) *Attorney, Agent, or Firm* — Mattingly & Malur, PC

(57) ABSTRACT

An underwater remote inspection device is provided with an etching device and a magnifying observation device mounted to a supporting member. A chamber of the etching device is provided with a negative electrode, a positive electrode and a sealing device, and is connected to an etchant supply pipe and an etchant exhaust pipe. A single pair of annular sealing members of the sealing device is provided to a distal end portion of the chamber. A suction passage formed in the side wall of the chamber communicates to a sealing region formed between the sealing members. The magnifying observation device is provided with a magnifying camera in a waterproof container and a plurality of LED lights are installed to the waterproof container. The underwater remote inspection apparatus can prevent leakage of an etchant and reduce execution time of etching.

4 Claims, 18 Drawing Sheets

UNDERWATER REMOTE INSPECTION DEVICE AND METHOD FOR UNDERWATER REMOTE INSPECTION

CLAIM OF PRIORITY

The present application claims priority from Japanese Patent application serial no. 2009-241370, filed on Oct. 20, 2009, the content of which is hereby incorporated by reference into this application.

BACKGROUND OF THE INVENTION

1. Technical Field

The present invention relates to an underwater remote inspection device and a method for underwater remote inspection, and more particularly, to an underwater remote inspection device and a method for underwater remote inspection suitable for inspecting a surface condition of a reactor internal of a boiling water reactor and a pressurized water reactor.

2. Background Art

As a device for inspecting the presence of a crack on a surface of a reactor internal installed in a nuclear reactor of a nuclear plant, an underwater remote inspection device has been known. Some examples of the underwater remote inspection device are described in Japanese Patent No. 3890239 and Japanese Patent Laid-open No. 2003-255074. The underwater remote inspection devices described in these publications have an etching device and a replica sampling device. The etching device includes electrode members and an electrolytic etchant supply device. An electrolytic etchant (oxalic acid) comes in contact with a surface to be inspected of a reactor internal, and the surface is etched by applying electricity to the electrode members. By etching the inspection surface of the reactor internal, the surface is corroded, making the grain boundaries of the metal structure of the surface easier to see. After the etching is completed, the replica sampling device is used to sample a replica of the etched surface.

Japanese Patent Laid-open No. 9(1997)-89786 discloses an underwater remote inspection device in which, an etchant (oxalic acid) soaked into a sponge is applied to a surface to be inspected of a reactor internal and the surface is etched. Using a magnifying camera provided to the underwater remote inspection device, an image is taken of the metal structure of the etched surface to be inspected of the reactor internal. The magnifying camera has a magnifying lens capable of enlarging the image to a few hundreds of times the standard, allowing the enlarged image of the metal structure to be taken. The image of the metal structure taken by the magnifying camera is displayed on a monitor so that any over sensitization in the inspection surface can be checked.

PRIOR ART LITERATURE

Patent Literature

Patent literature 1: Japanese Patent No. 3890239
Patent literature 2: Japanese Patent Laid-open No. 2003-255074
Patent literature 3: Japanese Patent Laid-open No. 9(1997)-89786

SUMMARY OF THE INVENTION

Technical Problem

When studying a cause of cracking occurred on a surface of a reactor internal of a nuclear reactor, it is important to check if the crack is extending along a grain boundary or not to determine whether the crack is an intergranular stress corrosion crack or not. For this reason, it has been preferred that the grain boundaries in the proximity of the crack be easily checked. As a method for checking the grain boundaries of a metal structure, electrolytic etching using an oxalic acid solution has been generally known. In a welding portion and a heat-affected zone in the vicinity of the welding portion, their corrosion resistance will be varied due to a high-temperature process of welding and dilution of the base metal and a welding metal, thus, the condition of electrolytic etching (current, voltage, a running time of the current, etc.) cannot be explicitly determined. For this reason, electrolytic etching of the metal surface and checking of the degree of etching of the metal surface are alternatively performed in actual work. In this case, since installation operation of an inspection device is repeatedly required, the etching work would take long time.

In the underwater remote inspection device disclosed in Japanese Patent Laid-open No. 9(1997)-89786, the degree of etching of the inspection surface of a reactor internal can be easily checked by looking at an image taken by the magnifying camera. However, since this underwater remote inspection device has a mechanism for applying the etchant to the inspection surface with a sponge, a size of the underwater remote inspection device is increased. The underwater remote inspection devices disclosed in Japanese Patent No. 3890239 and Japanese Patent Laid-open No. 2003-255074 for electrolytic etching are smaller than the underwater remote inspection device stated in Japanese Patent Laid-open No. 9(1997)-89786.

The inventors, thus, have come up with an idea to apply a magnifying camera to the underwater remote inspection device having an electrolytic etching mechanism (for example, see Japanese Patent No. 3890239 and Japanese Patent Laid-open No. 2003-255074). In this case, however, it has become clear that a new problem has emerged as shown below.

In the underwater remote inspection device described in Japanese Patent Laid-open No. 9(1997)-89786, a sponge provided to the distal end portion of an arm, soaked with an etchant is pressed onto the inspection surface of a reactor internal by extending the arm and the etchant soaked into the sponge is applied to the inspection surface. After the etching of the inspection surface of the reactor internal is completed, the arm is retracted to store the sponge inside a tightly-closed container. Since the pressing of the sponge onto the inspection surface of the reactor internal is done in front of a magnifying camera provided to the underwater remote inspection device, the degree of etching of the inspection surface can be observed by the magnifying camera when the sponge has been stored in the tightly-closed container.

In the underwater remote inspection device for electrolytic etching such as those described in Japanese Patent No. 3890239 and Japanese Patent Laid-open No. 2003-255074, electrodes are provided to a chamber, which is pressed onto the inspection surface of the reactor internal and supplied with an etchant inside. In order to improve the efficiency of etching of the inspection surface, the electrode should be disposed facing the etching execution surface of the inspection surface. This makes it difficult to install the magnifying camera to the chamber so as to make the camera facing the etching execution surface. The magnifying camera, thus, is required to be installed outside the chamber, facing the surface of the reactor internal, as the underwater camera shown in FIG. 9 of Japanese Patent Laid-open No. 2003-255074. In such a configuration, the chamber must be shifted upward (or downward) after etching is completed to position the magnifying camera facing the etching-completed etching execution surface and then, an image of the etching execution surface must be taken by the magnifying camera to check the degree of etching of the etching execution surface.

A sealing member is installed to a portion of the chamber of the etching device, the portion facing the surface of the reactor internal, to prevent the etchant in the chamber from leaking outside. When an image of the etching execution surface is to be taken by the magnifying camera, the etching device should be moved as soon as possible to reduce the execution time of etching. In consideration of such moving of the etching device, the airtightness between the chamber and the reactor internal is needed to prevent the etchant from leaking out of the chamber during etching, and the etching device should be swiftly moved to take an image of the etching execution surface.

It is an object of the present invention to provide an underwater remote inspection device and a method for underwater remote inspection that can prevent leakage of an etchant and reduce execution time of etching.

Solution to Problem

A feature of the present invention for attaining the above object is an underwater remote inspection device having a supporting member, and an etching device and a magnifying camera device mounted to the supporting member, wherein the etching device has a chamber mounted to the supporting member, electrode members provided to the chamber, an agent supply pipe for supplying an agent for etching, connected to the chamber to communicate to an etchant filling region formed in the chamber, and a sealing device provided to a distal end portion of the chamber, facing a surface of an inspection object, and wherein the sealing device has an annular first sealing member attached to the distal end portion of the chamber, an annular second sealing member surrounding the first sealing member, attached to the distal end portion of the chamber, and a pipe line communicated to a sealing region formed between the first and the second sealing members, connected to a suction apparatus for reducing the pressure in the region.

Since the sealing device has the annular first sealing member, the annular second sealing member surrounding the first sealing member, and the pipe line communicated to the region formed between the first and the second sealing members, connected to the suction apparatus for reducing the pressure in the region, the pressure in the region formed between the first and the second sealing members can be reduced after the distal end portions of the first and the second sealing members have come into contact with the surface of the inspection object. Consequently, the distal end portions of the first and the second sealing members are firmly pressed on the surface of the inspection object, and more tightly adhered to the surface of the inspection object. In this way, the chamber is reliably sealed inside and outside, and the agent supplied into the etchant filling region can be surely prevented from leaking out of the chamber.

In addition, the sealing device can be swiftly detached from the surface of the inspection object by raising the pressure in the region. Consequently, the magnifying camera device can be moved to the position of the etching-completed inspection area in a short period of time, reducing the execution time of etching.

Advantageous Effect Of The Invention

According to the present invention, leakage of the etchant can be prevented and the execution time of etching of the surface of the inspection object can be reduced.

DETAILED DESCRIPTION OF THE PREFERRED EMBODIMENTS

Embodiments of the present invention will be described below.

[Embodiment 1]

An underwater remote inspection method in embodiment 1, which is a preferred embodiment of the present invention, will be described with reference to the drawings.

Figure 1:
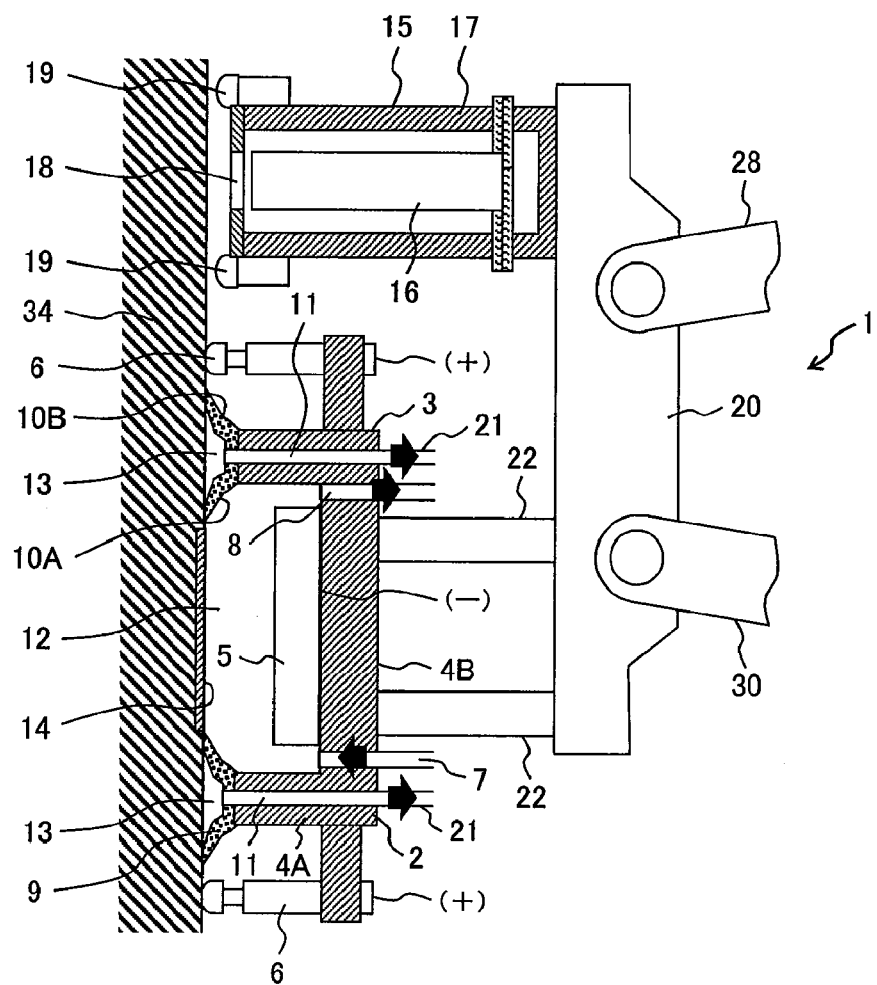
FIG. 1 is a longitudinal sectional view showing an underwater remote inspection device used in an underwater remote inspection method in embodiment 1, which is a preferred embodiment of the present invention.

An underwater remote inspection device 1 used in the present embodiment is, as shown in FIG. 1, provided with an etching device 2 and a magnifying observation device (a magnifying camera device) 15. The etching device 2 has a chamber 3, a negative electrode 5 and a positive electrode 6 as electrode members, an etchant supply pipe 7, an etchant exhaust pipe 8, and a sealing device 9. The magnifying observation device 15 has a magnifying camera 16, a waterproof container 17, and a plurality of LED lights (an illuminating device) 19. The etching device 2 and the magnifying observation device 15, or to be more specific, the chamber 3 and the waterproof container 17 are installed to a supporting member 20 provided to the underwater remote inspection device 1.

The chamber 3 is made up of a cylinder member 4A fixed to a plate member 4B. The plate member 4B is installed to a plurality of supporting members 22 fixed to the supporting member 20. In this way, the chamber 3 is held to the supporting member 20. An etchant filling region 12 surrounded by the cylinder member 4A and the plate member 4B is formed in the chamber 3. The negative electrode 5 is disposed in the etchant filling region 12 and attached to the plate member 4B. A plurality of positive electrodes 6 are disposed outside the chamber 3 and installed to the chamber 3. The etchant supply pipe 7 is fixed to the chamber 3 to communicate with the etchant filling region 12. The etchant exhaust pipe 8 is fixed to the chamber 3 to communicate with the etchant filling region 12.

The sealing device 9 has sealing members 10A and 10B and a suction passage 11. The sealing members 10A and 10B are each provided to an end portion of the cylinder member 4A, facing a surface to be inspected (an inspection surface) of an inspection object. The sealing members 10A and 10B each have a continuous annular shape, and are concentrically disposed to each other. The sealing member 10B is disposed outside the sealing member 10A, surrounding the sealing member 10A. A distal end portion of the sealing member 10A is curved inward from the chamber 3, and a distal end portion of the sealing member 10B is curved outward from the chamber 3. An annular sealing region 13 is formed between the sealing members 10A and 10B. The sealing region 13 surrounds the sealing member 10A and communicates to the suction passage 11 formed in the cylinder member 4A. The suction passage 11 communicates to a suction pipe 21 connected to the chamber 3.

The waterproof container 17 of the magnifying observation device 15 is installed to the supporting member 20. The magnifying observation camera 16 having a remote focus function is installed in the waterproof container 17, and a window 18 is formed in front of the magnifying camera 16 by fitting a sheet of glass to the waterproof container 17. The plurality of LED lights 19 is disposed outside the waterproof container 17 and installed to the waterproof container 17.

Figure 2:
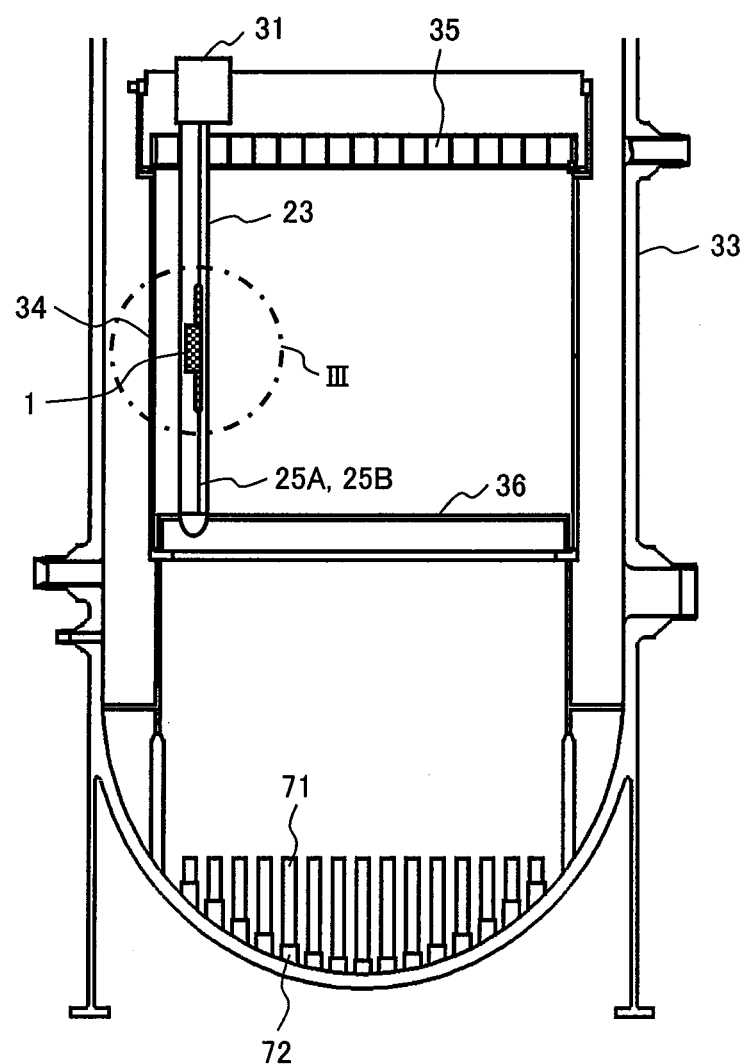
FIG. 2 is an explanatory drawing showing a state in which an underwater scanner storing the underwater remote inspection device shown in FIG. 1 is installed in a core shroud of a reactor pressure vessel.

The underwater remote inspection method in the present embodiment for inspecting a surface of an underwater inspection object, using the underwater remote inspection device 1 will be described below. In the underwater remote inspection method, the inspection object is a core shroud, which is a reactor internal provided in a reactor pressure vessel of a boiling water reactor. A general structure of the boiling water reactor will be described using FIG. 2. A boiling water reactor has a reactor pressure vessel 33, inside which a core (not shown) is disposed, and a cylindrical core shroud 34, an upper grid plate 35, a core plate 36, and so on are installed in the reactor pressure vessel 33. The core loaded with a plurality of fuel assemblies (not shown) is surrounded by the core shroud 34. In the core shroud 34, the upper grid plate 35 is disposed to an upper end portion of the core shroud 34 and installed to the core shroud 34. The core plate 36 is disposed below the upper grid plate 35 in the core shroud 34 and installed to the core shroud 34. A lower end portion of each fuel assembly loaded in the core is supported by the core plate 36 and an upper end portion of each fuel assembly is supported by the upper grid plate 35. A plurality of control rod drive mechanism housings (hereinafter, referred to as CRD housings) 71 is provided to the bottom portion of the reactor pressure vessel 33, penetrating the bottom portion. Each CRD housing 71 penetrates a stub tube 72 fixed to the bottom surface of the reactor pressure vessel 33 and attached to the stub tube 72.

The underwater remote inspection method is performed as one agenda of a periodic inspection performed after shutdown of operation of the boiling water reactor. After the shutdown of the operation of the boiling water reactor, a top head (not shown) of the reactor pressure vessel 33 is removed and the reactor pressure vessel 33 is opened up. Cooling water is filled in the reactor pressure vessel 33 and in a reactor well (not shown) located above the reactor pressure vessel 33. After the top head of the reactor pressure vessel 33 has been removed, a steam dryer (now shown) and a steam separator (not shown) installed above the upper grid plate 35 in the reactor pressure vessel 33 are sequentially removed and carried out of the reactor pressure vessel 33. Among the fuel assemblies loaded in the core, at least each of those found near the inner surface of the core shroud 34 is grasped by a fuel exchange apparatus (not shown), and then, this fuel assembly is taken out from the reactor pressure vessel 33 by the fuel exchange apparatus and transferred to a fuel storage pool (not shown).

After those fuel assemblies have been carried out of the core into the fuel storage pool, the underwater remote inspection method in the present invention is executed. To execute the underwater remote inspection of the inner surface of the core shroud 34, the underwater remote inspection device 1 should be transported into the core shroud 34. This transporting of the underwater remote inspection device 1 is achieved by moving an underwater scanning device 23 (see FIG. 2), in which the underwater remote inspection device 1 is stored, into the core shroud 34. A worker riding the fuel exchange apparatus, which runs on an operation floor (now shown) surrounding the reactor well, formed in a reactor building (not shown), transports the underwater scanning device 23 by using a tong to a region in the core shroud 34 below the upper grid plate 35 through a grid formed in the upper grid plate 35 while checking, on a TV monitor, an image around the underwater remote inspection device 1, taken by an underwater camera. A lower end portion of the underwater scanning device 23 is held to the core plate 36 (see FIG. 2). The underwater scanning device 23 held to the core plate 36 is in cooling water inside the reactor pressure vessel 33.

Figure 3:
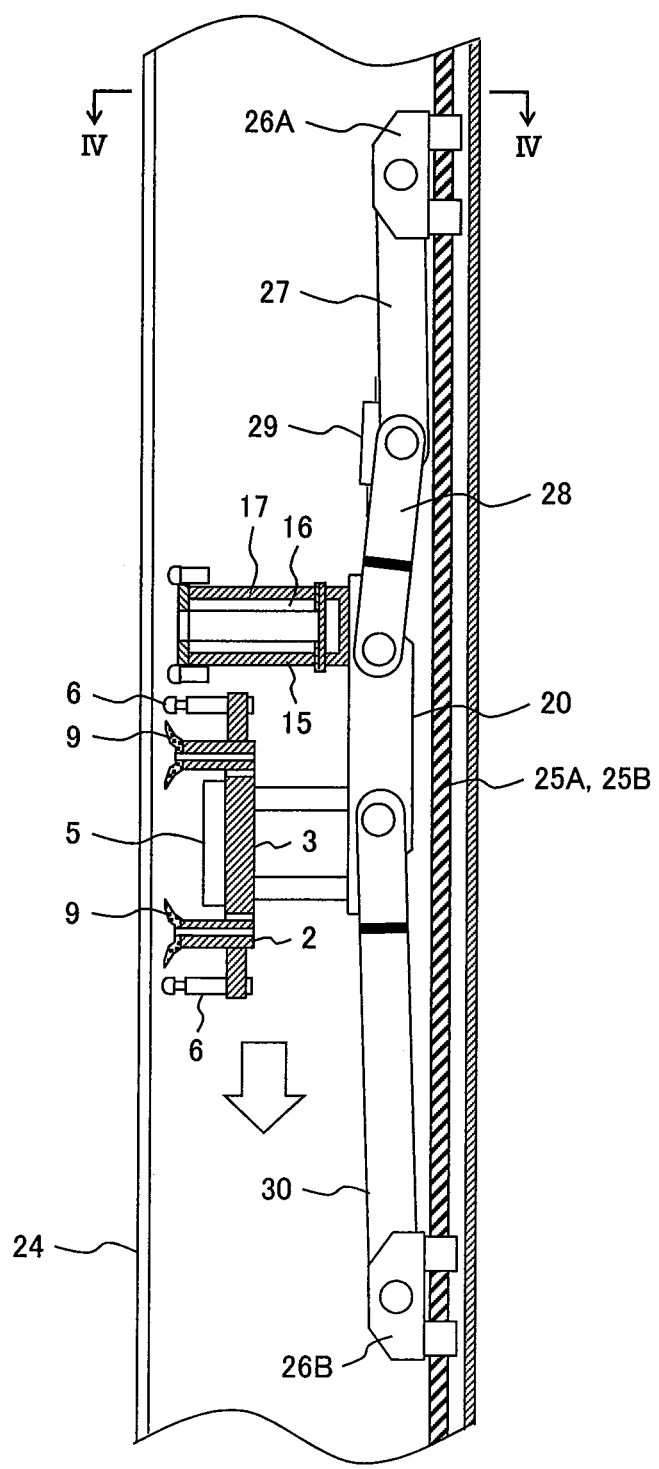
FIG. 3 is an enlarged view of part III in FIG. 2.
Figure 4:
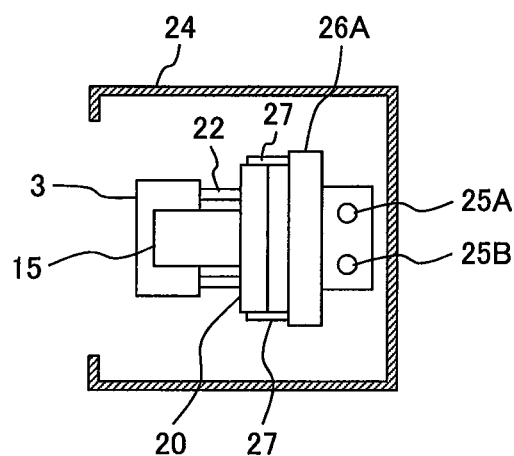
FIG. 4 is a sectional view taken along a line IV-IV of FIG. 3.
Figure 7:
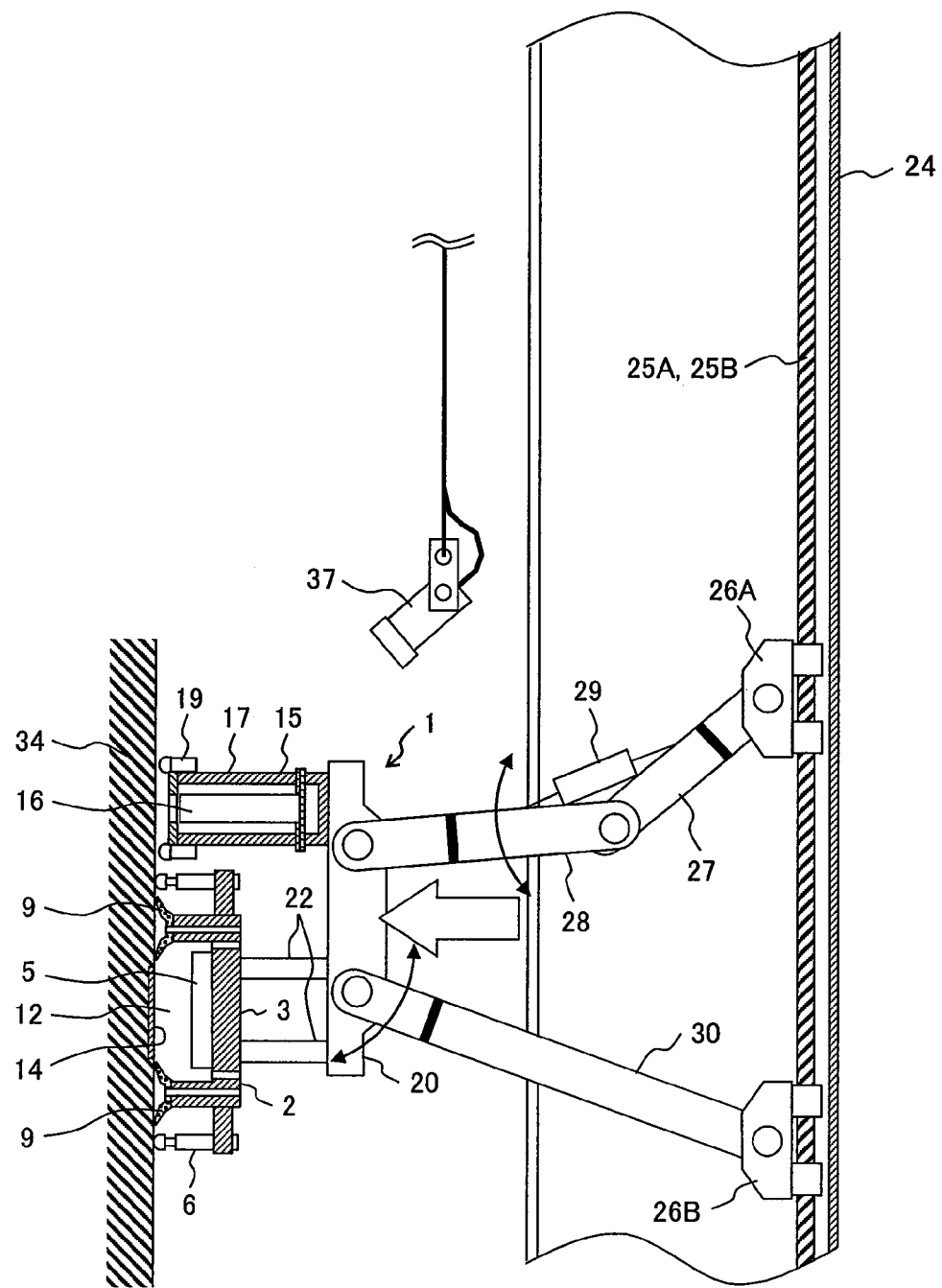
FIG. 7 is an enlarged view of part VII in FIG. 6.

Now, a structure of the underwater scanning device 23 will be described using FIG. 3. The underwater scanning device 23 has a casing 24, transporting rods 25A and 25B, moving bodies 26A and 26B, and motors (driving devices) 31. The motors are stepping motor. The casing 24 has a U-shaped cross section, practically having three side walls (see FIG. 4). One side surface of the casing 24 opens along an axial direction. Two motors 31 are installed to an upper end of the casing 24. Two transporting rods 25A and 25B are disposed side by side in the casing 24 (see FIG. 4), and the lower end portion of each of the transporting rods 25A and 25B is separately supported in the lower end portion of the casing 24 by one of two bearings (not shown) provided in the casing 24. A screw thread is formed on the surface of each of the transporting rods 25A and 25B. A rotating shaft of one motor 31 is coupled to an upper end of the transporting rod 25A. A rotating shaft of the other motor 31 is coupled to an upper end of the transporting rod 25B. The moving bodies 26A and 26B are disposed in the casing 24. The moving body 26A is engaged with the thread formed on the transporting rod 25A, and the moving body 26B with the thread formed on the transporting rod 25B. The transporting rod 25A penetrates through a through-hole formed in the moving body 26B and is not engaged with the moving body 26B. The transporting rod 25B penetrates through a through-hole formed on the moving body 26A and is not engaged with the moving body 26A. One end portion of a link 27 is rotatably attached to the moving body 26A with a pin. One end portion of a link 28 is rotatably coupled to the other end portion of the link 27 with a pin. A linear motor 29 is linked to the links 27 and 28 (see FIG. 7). One end of a link 30 is rotatably attached to the moving body 26B with a pin.

The underwater remote inspection device 1 is disposed in the casing 24. The other end portion of the link 28 is rotatably attached to the supporting member 20 of the underwater remote inspection device 1 with a pin. The other end portion of the link 30 is rotatably attached to the supporting member 20 with a pin.

While the lower end portion of the underwater scanning device 23 is held to the core plate 36, the motors 31 are located above the top surface of the upper grid plate 35. The underwater remote inspection method in the present embodiment after the lower end portion of the underwater scanning device 23 has been held to the core plate 36 will be specifically explained using FIG. 5.

The underwater remote inspection device is moved to the vicinity of an inspection area of an inspection object (step S1). The links 27 and 28, the supporting member 20, and the link 30 are practically parallel to the transporting rods 25A and 25B and a distance between the moving bodies 25A and 25B is the longest (see FIG. 3). The underwater remote inspection device 1 is completely stored in the casing 24 of the underwater scanning device 23. Also when the underwater scanning device 23 was passed through a grid of the upper grid plate 35, the underwater remote inspection device 1 has been stored in the casing 24 in the same manner. The two motors 31 of the underwater scanning device 23 are turned in the same direction at the same rotating speed. Since this turns the transporting rods 25A and 25B in the same direction at the same rotating speed, the moving bodies 25A and 25B can be moved downward while keeping their distance from each other between the moving bodies 25A and 25B. The etching device 2 and the magnifying observation device 15 are also moved downward simultaneously with the moving bodies 25A and 25B. When the chamber 3 of the etching device 2 reaches the position facing an inspection area (an inspection surface) 14 of the core shroud 34, which is a reactor internal that is an inspection object, the rotation of the two motors 31 is stopped to stop the moving bodies 25A and 25B from moving downward. In the step S1, the etching device 2 is moved downward to the level where the inspection area 14 is located in the core shroud 34.

For moving the moving bodies 25A and 25B in the axial direction of the core shroud 34, a nut rotatably installed to each of the moving bodies 25A and 25B may be turned instead of each motor 31. In this case, each motor 31 for turning each of the transporting rods 25A and 25B becomes no longer necessary, and the transporting rods 25A and 25B are not turned. The nut provided to each of the moving bodies 25A and 25B is engaged with the respective transporting rod, and each nut is turned by a motor provided to each of the moving bodies 25A and 25B, through a gear.

Figure 6:
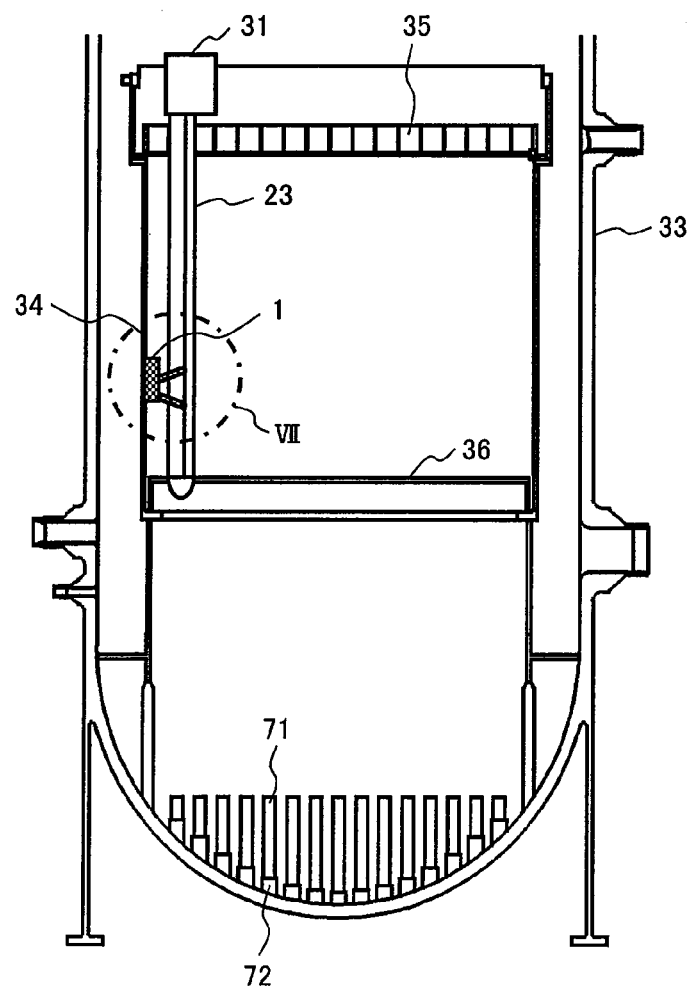
FIG. 6 an explanatory drawing showing a state in which an underwater remote inspection apparatus shown in FIG. 1 is pressed on an inner surface of a core shroud.

The underwater remote inspection device is moved in the horizontal direction (step S2). The two motors 31 are turned at the same rotating speed in an opposite directions from each other. The transporting rod 25A is turned to move the moving body 26A downward and the transporting rod 25B is turned to move the moving body 26B upward in the opposite direction from the transporting rod 25A. The distance from each other between the moving bodies 25A and 25B is reduced, and the etching device 2 supported by each moving body with the link moves outward from the casing 24, moving in the horizontal direction toward the inspection area 14 of the core shroud 34. This moving of the etching device 2 is performed while an image from an underwater camera 37 (see FIG. 7) is being checked on a TV monitor. When the distal end portions of the sealing members 10A and 10B of the sealing device 9 provided to the chamber 3 are pressed on the inner surface of the core shroud 34 (see FIGS. 6 and 7), the two motors 31 are stopped to stop the etching device 2 from moving in the horizontal direction. At this time, the sealing members 10A and 10B are surrounding the inspection area 14, and cooling water is present in the etchant filling region 12 and the sealing region 13. The plurality of positive electrodes 6 come into contact with the surface of the core shroud 34.

When the etching device 2 is tilted in relation to the central axis of the core shroud 34, the linear motor 29 is driven before the distal end portions of the sealing members 10A and 10B are pressed on the inner surface of the core shroud 34, to adjust the angle that the links 27 and 28 make, positioning the chamber 3 parallel to the central axis of the core shroud 34. In this way, the orientation of the underwater remote inspection device 1 can be adjusted.

The position of the etching device 2 while the chamber 3 is covering the inspection area 14 by having the distal end portions of the sealing members 10A and 10B pressed onto the inner surface of the core shroud 34 is set to a point zero. The coordinate position of the point zero is shown by a coordinate in a circumferential direction of the core shroud 34 (x-coordinate) and a coordinate in the axial direction of the core shroud 34 (y-coordinate). The x-coordinate is determined by the position, in the circumferential direction of the core shroud 34, of the grid of the upper grid plate 35 through which grid the underwater scanning device 23 is inserted. The y-coordinate is obtained by a computer (not shown) based on an output signal of an encoder (not shown) provided to each of the two motors 31. The x- and y-coordinates of the point zero are stored in a memory of the computer.

Seal between the etching device and the inspection object is performed (step S3). A pump (a suction apparatus, not shown) connected to the suction pipe 21 is driven. Cooling water in the sealing region 13 formed between the inner surface of the core shroud 34 and the sealing members 10A and 10B pressed onto the inner surface of the core shroud 34 is sucked by the drive of the pump connected to the suction pipe 21. This reduces the pressure in the sealing region 13 lower than the pressure outside the sealing members 10A and 10B, tightly adhering each distal end portion of the sealing members 10A and 10B onto the inner surface of the core shroud (the inspection object) 34.

The inspection area is electrolytically etched (step S4). An etchant (for example, a 10% oxalic acid aqueous solution) filled in a bath tank (not shown) is supplied, by opening a valve, into the etchant filling region 12 formed by the surrounding chamber 3 and the core shroud 34, through a bath hose (not shown) and the etchant supply pipe 7 connected to the bath hose. The etchant is injected into the etchant filling region 12 while an exhaust pump (not shown) connected to an exhaust hose (not shown) connected to the etchant exhaust pipe 8 is driven to discharge the cooling water in the etchant filling region 12. The bath tank is placed on the operation floor. The etchant is filled in the etchant filling region 12, coming into contact with the inspection area 14 of the core shroud 34. Then, a direct current is applied between the negative electrode 5 and the positive electrodes 6 for a predetermined period of time. The direct current passes through the positive electrodes 6, the inspection area 14, the etchant in the etchant filling region 12, and the negative electrode 5. Due to the action of the direct current and the etchant, the surface of the inspection area (the surface come into contact with the etchant) is electrolytically etched to corrode the grain boundaries of the metal structure of the surface of the inspection area 14.

The sealing between the etching device and the inspection object is removed (step S5). By switching a valve, the etchant supply pipe 7 is connected to a pure water tank instead of the bath tank. The exhaust pump connected to the exhaust hose is driven to suck the etchant in the etchant filling region 12, and the etchant is discharged to a waste solution tank (not shown) through the exhaust hose. The operation of the exhaust pump supplies pure water in the pure water tank into the etchant filling region 12 through the etchant supply pipe 7. The pure water supplied into the etchant filling region 12 also is discharged to the waste solution tank through the exhaust hose. This waste solution tank is placed on the operation floor. The pure water is supplied into the etchant filling region 12 for a predetermined period of time to completely discharge the etchant in the etchant filling region 12 from the etchant filling region 12.

After the predetermined period of time has passed, cooling water is supplied into the sealing region 13 through the suction pipe 21. The cooling water is supplied by stopping the operation of the pump connected to the suction pipe 21 and opening a valve provided to a branching pipe of the suction pipe 21 to communicate the sealing region 13 with a region outside the chamber 3 in the core shroud 34. This allows the cooling water in the core shroud 34 to flow through the suction pipe 21 into the sealing region 13 having a low pressure. The pressure in the sealing region 13 is recovered, the pressing force of the sealing members 10A and 10B onto the inner surface of the core shroud 34 is released, and the etching device 2 becomes easier to be detached from the core shroud 34. The branching pipe provided with the above valve is a pressure recovery apparatus for the sealing region 13.

Figure 8:
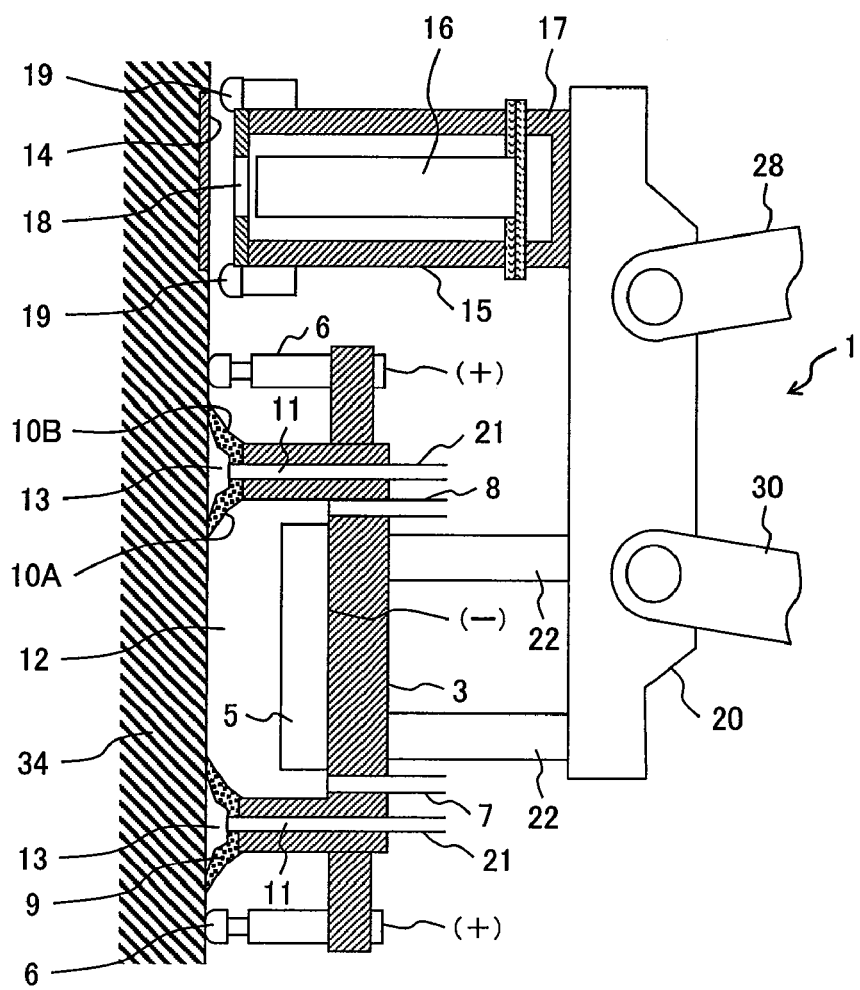
FIG. 8 is an explanatory drawing showing a state of an underwater remote inspection device after completion of step S6 shown in FIG. 5.

The magnifying observation device 15 is moved to the inspection area (step S6). In the state shown in FIG. 7, the two motors 31 are turned in the opposite directions from each other at the same rotating speed to slightly shift the chamber 3 in the horizontal direction, detaching the distal end portions of the sealing members 10A and 10B from the inner surface of the core shroud 34. Then, the two motors 31 are turned in the same direction at the same rotating speed to move the moving bodies 26A and 26B downward while keeping the distance from each other between the moving bodies 26A to 26B. When the magnifying observation camera 16 reaches the position facing the inspection area 14 (see FIG. 8), the moving bodies 26A and 26B are stopped from being moved downward. An image of the inspection area 14 after etching is taken by the magnifying observation camera 16. When the image of the inspection area 14 is to be taken, the focus of the magnifying observation camera 16 is adjusted. This focus adjustment is achieved by, first, roughly setting the location of the magnifying observation camera 16 by turning the transporting rods 25A and 25B in the opposite directions and moving the underwater remote inspection apparatus 1 in the horizontal direction, then, by finely adjusting the focus with a remote focus. When the magnifying observation camera 16 is tilted in relation to the central axis of the core shroud 34, i.e., to the surface of the inspection area 14, as described before, the linear motor 29 is driven to adjust the orientation (an angle) of the magnifying observation device 15 to focus the magnifying observation camera 16.

The inspection area is observed under magnification (step S7). Light emitted from the plurality of LED lights 19 is irradiated on the etched inspection area 14. The inspection area 14 is diagonally irradiated from the LED lights 19. The magnifying observation camera 16 takes an image of the inspection area 14 and outputs the obtained image data to, for example, a TV monitor (a display device) placed on the operation floor.

Whether it is possible to distinguish a crack from the grain boundaries of the metal structure of the inspection area is determined (step S8). An operator looks at the image of the etched inspection area 14, displayed on the TV monitor, and determines whether the grain boundaries of the metal structure of the inspection area 14 and a crack that occurred in the grain boundaries are distinguishable. If the degree of electrolytic etching of the inspection area 14 is appropriate, the grain boundaries of the metal structure can be confirmed by eye, and when there is a crack in the inspection area 14, the crack can be easily distinguished from the grain boundaries. When the grain boundaries and a crack are distinguishable, it is determined as "Yes" in the step S8. When the operator determines that the grain boundaries and a crack are not distinguishable in the step S8, the determination in the step S8 will be "No".

When the determination in the step S8 is "No", the operator determines if it is over-etched or not based on the image of the etched inspection area 14, displayed on the TV monitor (Step S9). When the determination in the step S9 is "No", it means that the degree of etching is not enough, thus, the operations of the steps S1 to S4 are repeated to electrolytically etch the inspection area 14 again, followed by the operations of the steps S5 to S8. When the determination in the step S9 is "Yes", the etched inspection area 14 is too over-etched to distinguish between the grain boundaries and a crack. In this case, the etched inspection area 14 is mirror polished (step S10). To the mirror-polished inspection area 14, the operations of the steps S1 to S8 are repeated.

The enlarged image of the inspection area is recorded (step S11). When the determination in the step S8 becomes "Yes", the enlarged image of the inspection area 14 taken by the magnifying observation camera 16 is recorded in a memory of the above-mentioned computer.

The magnifying observation device is moved away from the surface of the inspection object (step S12). The two motors 31 are turned in the opposite directions from the rotating directions of the transporting rods 25A and 25B in the step S2 to turn the transporting rods 25A and 25B in the opposite directions from each other at the same rotating speed. The moving bodies 26A and 26B are moved along the transporting rods 25A and 25B in the direction away from each other. This moves the underwater remote inspection device 1 away from the core shroud (the inspection object) 34 in the horizontal direction. The magnifying observation device 15 also is moved away from the core shroud 34. The distance between the moving bodies 26A and 26B is further expanded, and the underwater remote inspection device 1 is stored in the casing 24 of the underwater scanning device 23 as shown in FIG. 3.

The underwater remote inspection device is moved away from the position facing the inspection area (step S13). The two motors 31 are driven to turn the transporting rods 25A and 25B in the opposite direction from the step S1 at the same rotating speed. The moving bodies 26A and 26B move upward, moving the underwater remote inspection device 1 upward as well.

When there is another inspection area 14 above the previously-described inspection area 14, the moving bodies 26A and 26B are moved to move the underwater remote inspection device 1 upward in the same manner as in the step S13. The etching device 2 of the underwater remote inspection device 1 is brought to face the other inspection area 14. To this inspection area 14, each operation described above shown in FIG. 5 is performed.

The underwater remote inspection device is retrieved from the reactor pressure vessel (step S14). After the etching is completed for the inspection areas 14 on the inner surface of the core shroud 34 in the axial direction of the core shroud 34 while the underwater scanning device 23 is inserted through the grid of the upper grid plate 35 described above, the underwater remote inspection device 1 is taken out from the reactor pressure vessel 33. This removal of the underwater remote inspection device 1 is done by a worker using a tong.

Figure 5:
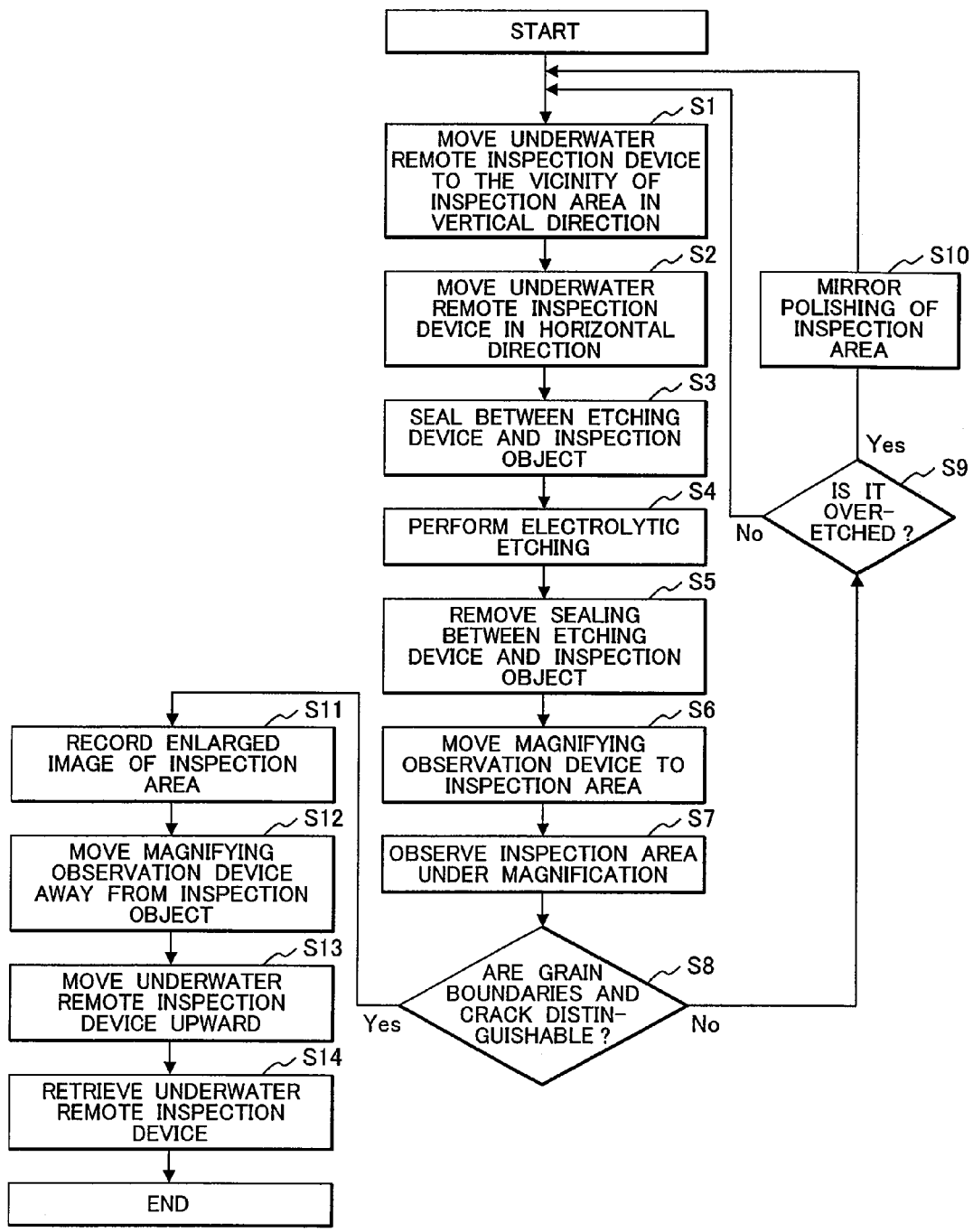
FIG. 5 is a flowchart showing processes of an underwater remote inspection method in embodiment 1 using the underwater remote inspection device shown in FIG. 1.

When there is an inspection area 14 in the other location on the inner surface of the core shroud 34 in the circumferential direction of the core shroud 34, the underwater scanning device 23 storing the underwater remote inspection device 1 is inserted into the grid of the upper grid plate 35, which is the grid closest to the location of the inspection area in the circumferential direction of the core shroud 34. The underwater scanning device 23 is held by the core plate 36. Then each operation shown in FIG. 5 is performed.

In the present embodiment, the sealing device 9 of the chamber 3, provided to the portion facing the inspection object (the core shroud), has a double structure including the annular sealing members 10A and 10B, and the sealing region 13 formed between the sealing members 10A and 10B communicates with the suction passage 11 formed in the side wall of the chamber 3. For this reason, when the distal end portions of the sealing members 10A and 10B are pressed onto the inner surface of the core shroud 34, the cooling water in the sealing region 13 can be pumped out through the suction passage 11, reducing the pressure in the sealing region 13 lower than the pressure of the cooling water outside the chamber 3 and the pressure in the etchant filling region 12. The distal end portions of the sealing members 10A and 10B are firmly pressed onto the inner surface of the core shroud 34, more tightly adhered onto the inner surface of the core shroud 34. The inside and outside sealing of the chamber 3 can be reliably achieved by the sealing members 10A and 10B, and leakage of the etchant supplied into the etchant filling region 12 to the outside of the chamber 3 can be surely prevented. In addition, if by any chance, the etchant in the etchant filling region 12 leaks out to the sealing region 13 through the joint between the sealing member 10A and the core shroud 34, the leaked etchant will be sucked into the suction pipe 21, allowing nothing to leak out of the chamber 3 through the joint between the sealing member 10B and the core shroud 34.

The present embodiment is provided with the magnifying observation camera 16, allowing the magnifying observation camera 16 to take an image of the grain boundaries of the metal structure in the inspection area 14 after being etched by the etching device 2, so that the degree of etching of the inspection area 14 can be checked swiftly. This can shorten the executing time of etching.

When the image is to be enlarged to the level that allows observation of the structure of the grain boundaries, only a small range is available for a point (a distance and an angle) to which the magnifying observation camera 16 can focus with a remote focus. However, the orientation of the magnifying observation camera 16 can be adjusted by the operation of the linear motor 29 to correct tilting of the camera in relation to the central axis of the core shroud 34, so that the magnifying observation camera 16 can be easily focused by the operation of the linear motor 29 and the image of the grain boundaries in the inspection area 14 can be clearly taken.

In the present embodiment, since the circular negative electrode 5 provided to the chamber 3 of the etching device 2 is facing the inspection area 14, the inspection area 14 can be etched effectively. The magnifying observation camera 16 is provided to the outside of the chamber 3 because it cannot be disposed in the chamber 3 due to the installation of the negative electrode 5. For this reason, the underwater remote inspection device 1 is moved to take an image of the etched inspection area 14 by the magnifying observation camera 16. In the present embodiment, as described above, while the distal end portions of the sealing members 10A and 10B are tightly adhered onto the inner surface of the core shroud 34 to seal between the chamber 3 and the core shroud 34 using the double structure of the sealing members 10A and 10B and the suction passage 11, the sealing between them can be quickly released by raising the pressure in the sealing region 13. Consequently, the magnifying observation camera 16 can be moved to the etched inspection area 14 in a short period of time from the time when etching is completed.

The etching is performed using the electrodes and the etchant so that the underwater remote inspection device 1 can be downsized. This allows the underwater remote inspection device 1 to inspect a surface of a structural member, facing a narrow portion in the reactor pressure vessel 33.

[Embodiment 2]

Figure 9:
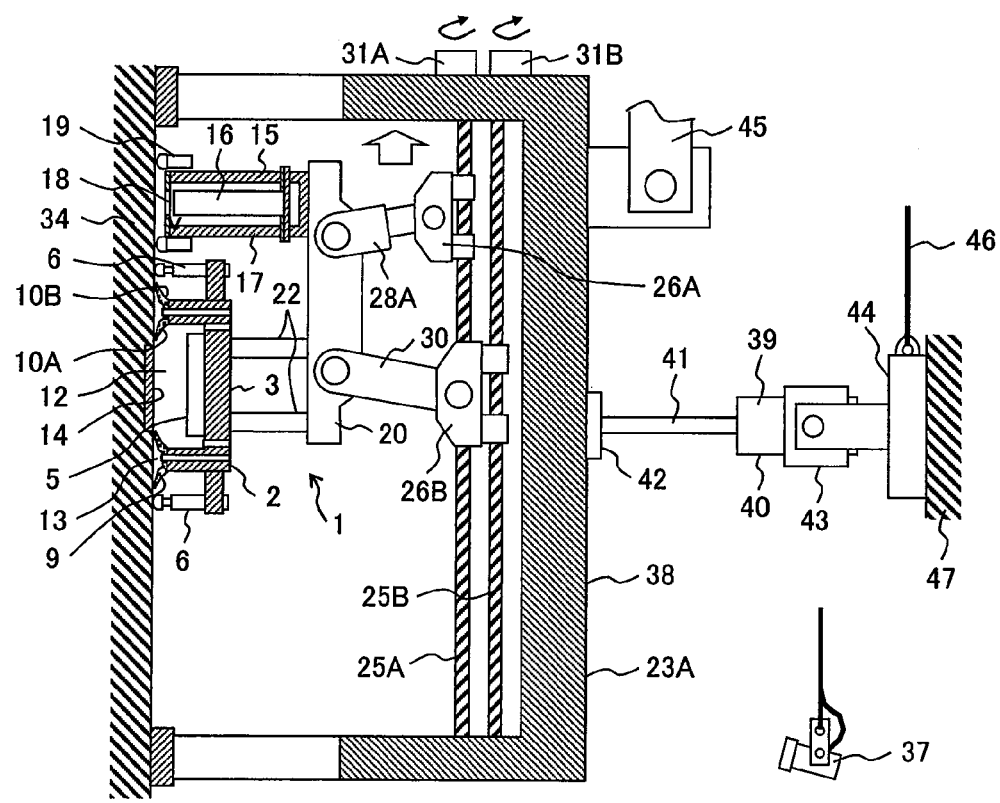
FIG. 9 is a longitudinal sectional view showing an underwater remote inspection device and an underwater scanning device used in an underwater remote inspection method in embodiment 2, which is another embodiment of the present invention.
Figure 10:
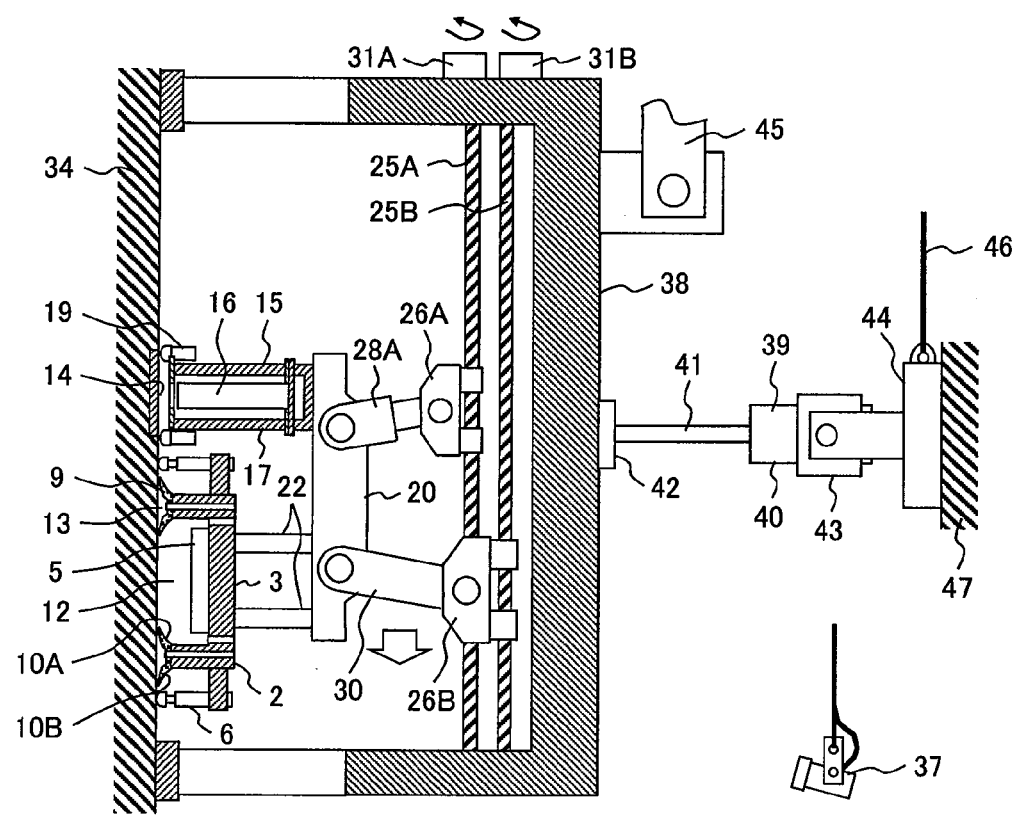
FIG. 10 is an explanatory drawing showing a state of an underwater remote inspection device after completion of step S6 in an underwater remote inspection method in embodiment 2.

An underwater remote inspection method in embodiment 2, which is another embodiment of the present invention, will be described using FIGS. 9 and 10. In the present embodiment, the underwater remote inspection device 1 used in embodiment 1 is used. An underwater scanning device 23A is used to move the underwater remote inspection device 1 in the present embodiment. The underwater scanning device 23A has the transporting rods 25A and 25B, the moving bodies 26A and 26B, motors (driving devices) 31A and 31B, and a casing 38. The motors 31A and 31D are stepping motor. A screw thread is formed on the surface of each of the transporting rods 25A and 25B, which are disposed in the casing 38 and rotatably attached to the casing 38. The transporting rod 25A is coupled to the rotating axis of the motor 31A, and the transporting rod 25B to the rotating axis of the motor 31B. The moving body 26A is engaged with the thread of the transporting rod 25A, and the moving body 26B with the thread of the transporting rod 25B. The link 30 rotatably attached to the supporting member 20 of the underwater remote inspection device 1 is coupled to the moving body 26B. A link 28A is rotatably attached to each of the supporting member 20 and the moving body 26A. The underwater remote inspection device 1 is stored in the casing 38.

A worker holds a tong 45 attached to the casing 38 and lowers the underwater scanning device 23A holding the underwater remote inspection device 1 in the reactor pressure vessel 33 without the top head, filled with cooling water. The underwater scanning device 23A is passed through a grid of the upper grid plate 35 and reaches the position facing the inspection area 14 on the inner surface of the core shroud 34. The underwater scanning device 23A is pressed onto the inner surface of the core shroud 34 by a fixing device 39. At this time, the sealing member 10A of the sealing device 9 is surrounding the inspection area 14.

The fixing device 39 has a cylinder 40, a rod 41, and a pressing plate 42. The rod 41 is coupled to a piston (not shown) in the cylinder 40. The pressing plate 42 is fixed to the distal end of the rod 41. The cylinder 40 is attached to a supporting member 43 attached to a pressing plate 44. A tong 46 is attached to the supporting member 43.

Before the underwater scanning device 23A is carried into the reactor pressure vessel 33, a plurality of fuel assemblies located in front of the inspection area 14 has been carried out of the reactor pressure vessel 33. A metallic supporting post 47 is carried by a fuel exchange apparatus to the region in the core shroud 34 where the fuel assemblies have been removed. The lower end portion of the supporting post 47 is held by the core plate 36 and the upper end portion of the supporting post 47 by the upper grid plate 35.

A worker holds the tong 46 and transports the fixing device 39 in the core shroud 34. The fixing device 39 is disposed between the supporting post 47 and the underwater scanning device 23A that has reached the position facing the inspection area 14. The pressing plate 44 comes into contact with one side surface of the supporting post 47, and high-pressure water is supplied into the cylinder 40 through a high-pressure hose connected to the cylinder 40. The piston in the cylinder 40 moves to move the rod 41 toward the underwater scanning device 23A. The pressing plate 42 comes into contact with the casing 38 of the underwater scanning device 23A to press the casing 38 onto the inner surface of the core shroud 34. In this way, the underwater scanning device 23A is pressed onto and fixed to the inner surface of the core shroud 34 by the fixing device 39.

In the underwater remote inspection method in the present embodiment also, each process shown in FIG. 5 performed in embodiment 1 is performed. However, the underwater remote inspection device 1 in the present embodiment is moved in the axial and the horizontal directions of the core shroud 34 in the following ways. The underwater remote inspection device 1 is moved in the axial direction of the core shroud 34 along the transporting rods 25A and 25B by turning the motors 31A and 31B in the same direction at the same rotating speed. By turning the motors 31A and 31B in the opposite directions at the same rotating speed, the underwater remote inspection device 1 is moved in the horizontal direction.

Each effect attained in embodiment 1 can also be obtained in the present embodiment.

[Embodiment 3]

An underwater remote inspection method in embodiment 3, which is another embodiment of the present invention, will be described with reference to the drawings.

Figure 11:
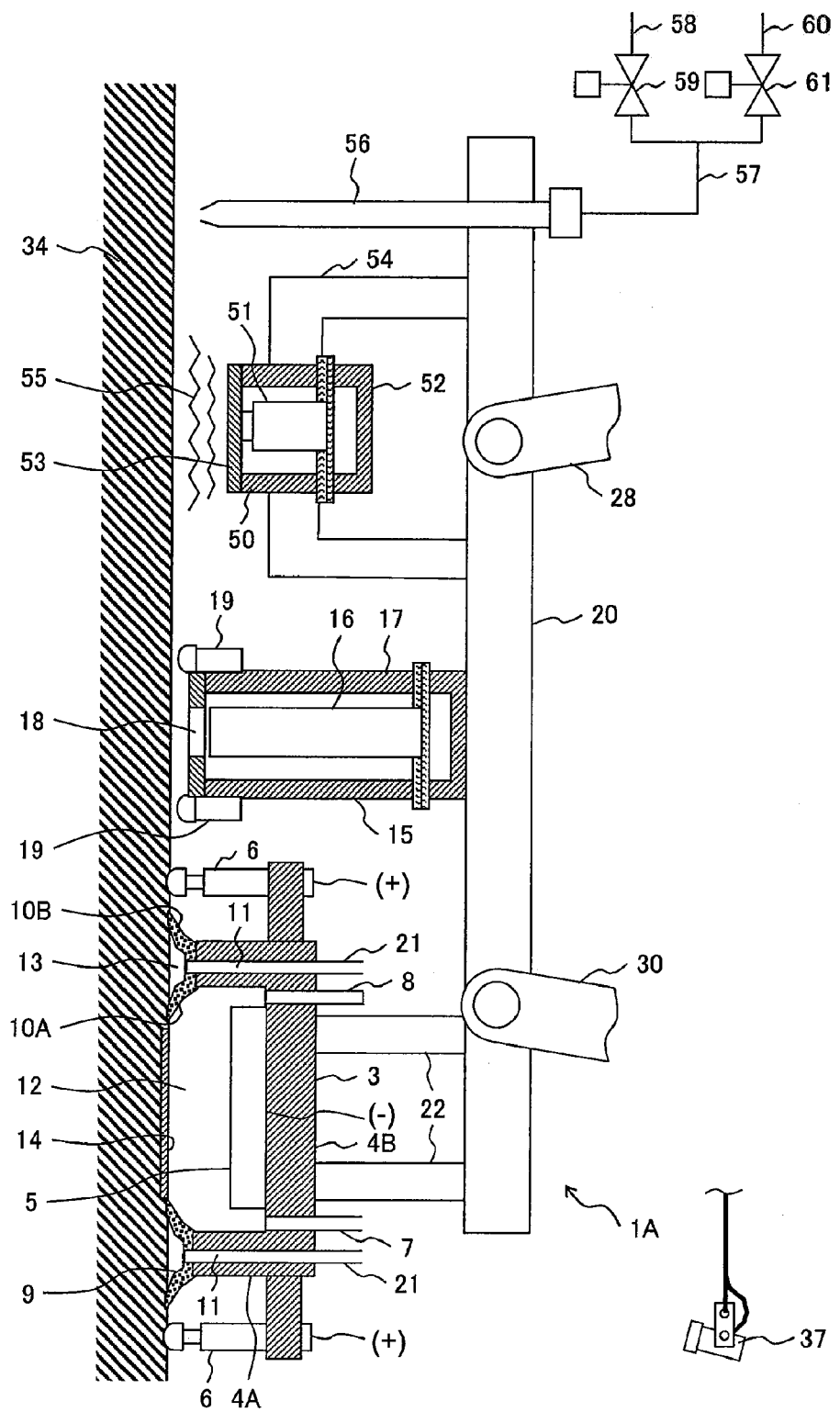
FIG. 11 is a longitudinal sectional view showing an underwater remote inspection device used in an underwater remote inspection method in embodiment 3, which is another embodiment of the present invention.

An underwater remote inspection device 1A (see FIG. 11) used in the present embodiment has a structure in which an ultrasonic cleaning device 50 is added to the underwater remote inspection device 1. The other structures of the underwater remote inspection device 1A are the same as the underwater remote inspection device 1.

The ultrasonic cleaning device 50 has an ultrasonic oscillator 51, a waterproof container 52, and an ultrasonic diaphragm 53. The ultrasonic cleaning device 50 is disposed above the magnifying observation device 15. The ultrasonic oscillator 51 is installed in the waterproof container 52 provided to a supporting member 54 attached to the supporting member 20. The ultrasonic diaphragm 53 is disposed in front of the ultrasonic oscillator 51 and attached to the waterproof container 52. The ultrasonic diaphragm 53 is facing the surface of the inspection object (for example, the core shroud 34). A nozzle 56 is disposed in the proximity of the ultrasonic cleaning device 50 and attached to the supporting member 20. A high pressure hose 57 is connected to the nozzle 56. A water supply hose 58 provided with an opening/closing valve 59 and a water suction hose 60 provided with an opening/closing valve 61 are connected to the high pressure hose 57.

Figure 12:
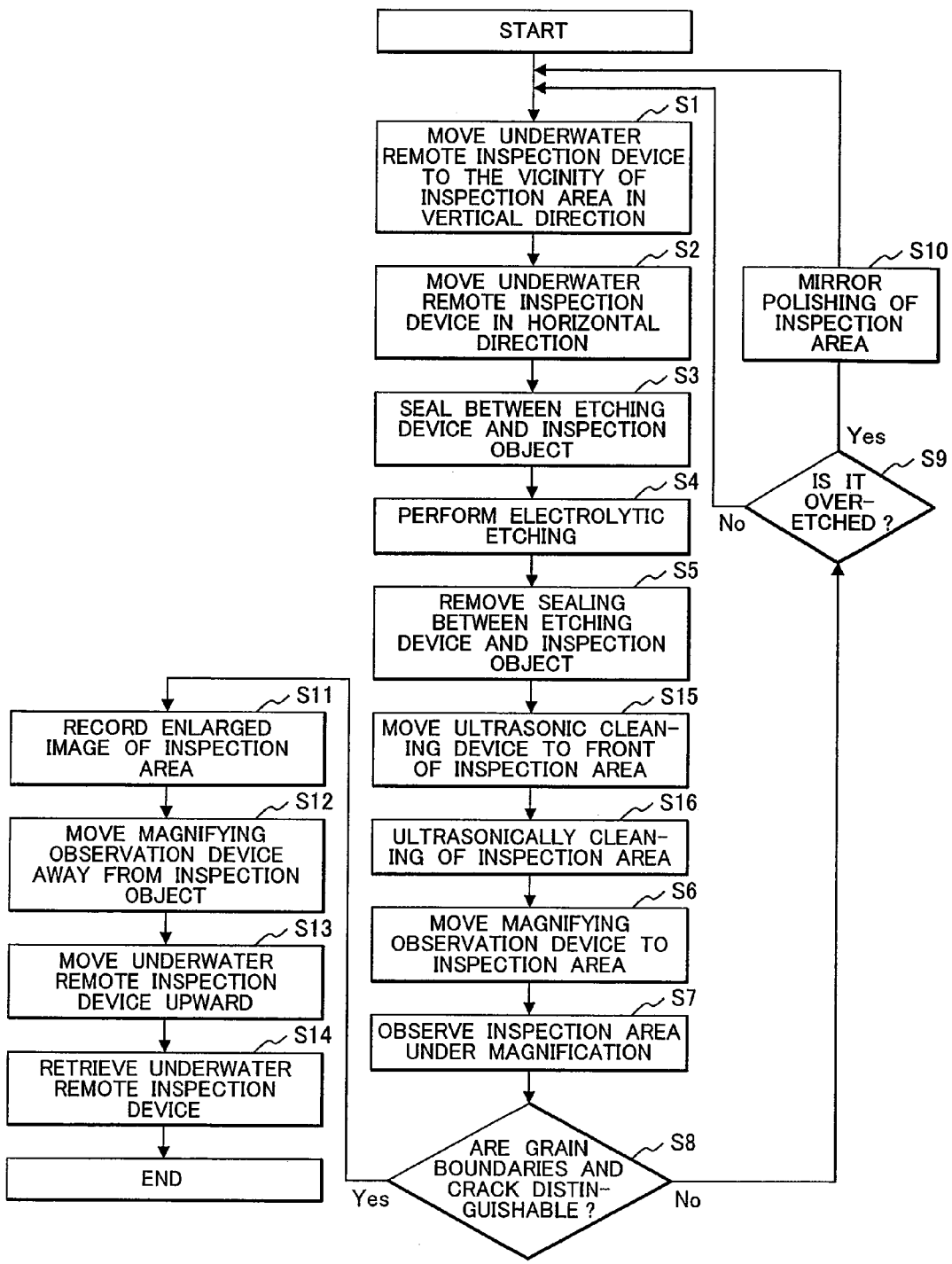
FIG. 12 is a flowchart showing processes of an underwater remote inspection method in embodiment 3 using an underwater remote inspection device shown in FIG. 11.

In the underwater remote inspection method in the present embodiment, each process shown in FIG. 12 is performed. The processes of the underwater remote inspection method shown in FIG. 12 are the processes of the underwater remote inspection method shown in FIG. 5 performed in embodiment 1 with the addition of each process of the steps S15 and S16. The steps S15 and S16 are performed between the steps S5 and S6.

In the underwater remote inspection method in the present embodiment, the ultrasonic cleaning device is moved to the front of the inspection area (step S15) after each processes of the steps S1 to S5 has been performed. The two motors 31 are driven to turn each motor 31 in the same direction at the same rotating speed so that the transporting rods 25A and 25B are turned in the same direction at the same rotating speed. The underwater remote inspection apparatus 1A moves downward, and the ultrasonic cleaning device 50 is moved to the position facing the etched inspection area 14 of the core shroud 34, which is the inspection object.

The inspection area is ultrasonically cleaned (step S16). The ultrasonic oscillator 51 is vibrated to propagate oscillating waves to the ultrasonic diaphragm 53. The ultrasonic diaphragm 53 vibrates to generate an ultrasonic wave 55. This ultrasonic wave 55 propagates through cooling water and hits the etched inspection area 14. Extraneous matter adhered on the surface of the inspection area 14 is removed by the ultrasonic wave 55. In this way, the surface of the inspection area 14 is ultrasonically cleaned. The extraneous matter detached from the surface is sucked, with the cooling water in the core shroud 34, into the nozzle 56 by opening the opening/closing valve 61 and driving a pump (not shown) connected to the water suction hose 60, to be discharged through the water suction hose 60. The opening/closing valve 59 may be opened instead of the opening/closing valve 61 and a pump (not shown) connected to the water supply hose 58 may be driven to eject pressurized water from the nozzle 56. It is the operator's choice whether to open the opening/closing valve 61 or 59.

After the process of the step S16 is completed, each process of the steps S6 to S8 is performed. When the determination in the step S8 is "No", the determination of the step S9 is performed, and when the determination in the step S9 is "No", each process of the steps S1 to S5, S15, S16, and S6 to S8 is performed. When the determination in the step S9 is "Yes", each process of the steps S10, S1 to S5, S15, S16, and S6 to S8 is performed. When the determination in the step S8 is "Yes", each process of the steps S11 to S14 is performed.

Each effect attained in embodiment 1 can also be obtained in the present embodiment. Since the inspection area 14 is ultrasonically cleaned in the present embodiment, the image of the inspection area 14 taken by the magnifying observation camera 16 will be clearer. Consequently, the degree of etching of the inspection area 14 can be distinguished with better accuracy.

[Embodiment 4]

An underwater remote inspection method in embodiment 4, which is another embodiment of the present invention, will be described with reference to the drawings.

Figure 13:
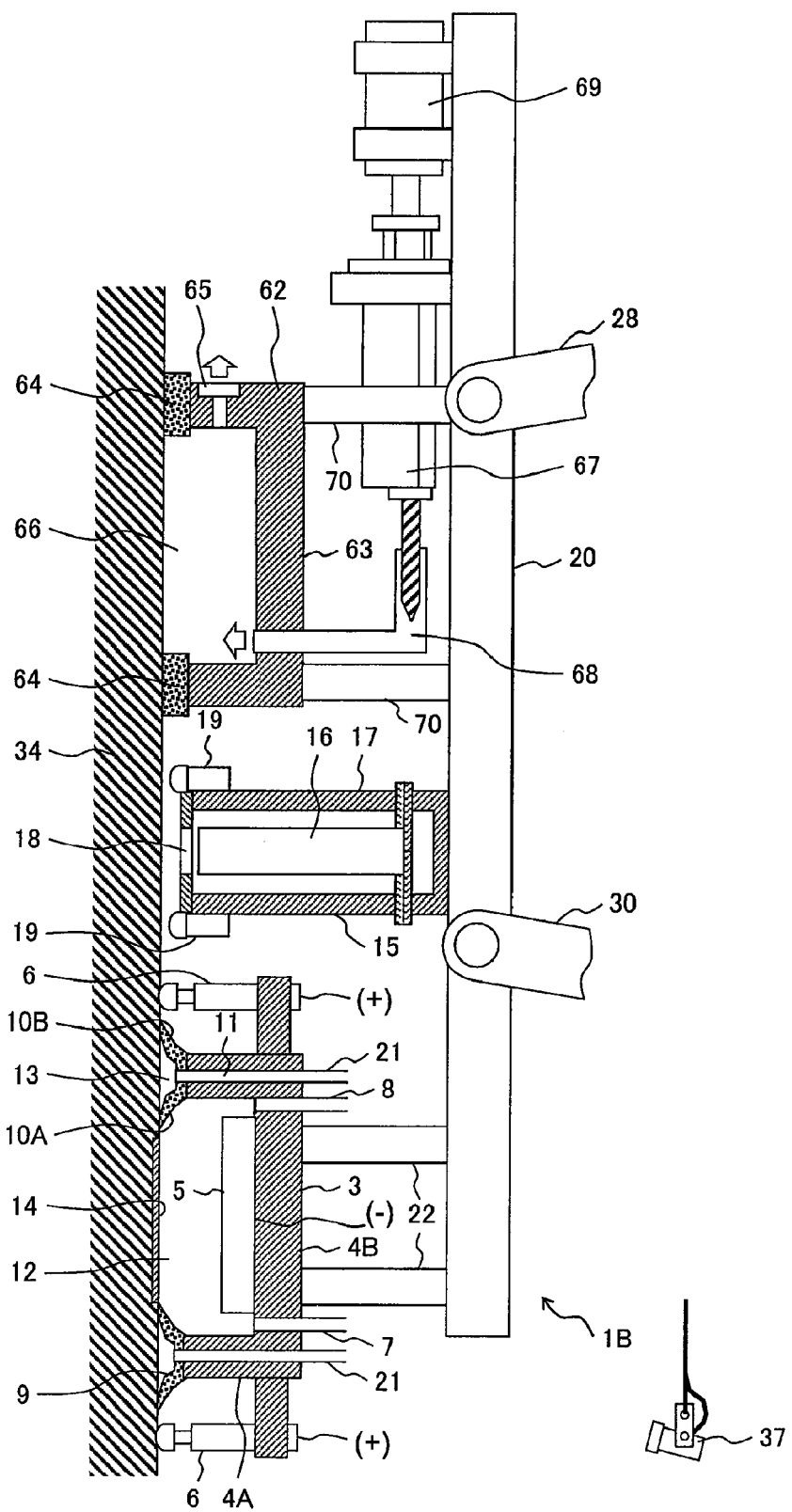
FIG. 13 is a longitudinal sectional view of an underwater remote inspection device used in an underwater remote inspection method in embodiment 4, which is another embodiment of the present invention.

An underwater remote inspection device 1B (see FIG. 13) used in the present embodiment has a structure in which a replica sampling device 62 is added to the underwater remote inspection device 1. The other structures of the underwater remote inspection device 1B are the same as the underwater remote inspection device 1.

The replica sampling device 62 is provided with a replica sampling head 63, a replica agent cartridge 67, a replica agent supply pipe 68, and a hydraulic cylinder 69, and disposed above the magnifying observation device 15. The replica sampling head 63 is attached to the supporting member 20 with a plurality of supporting members 70. The replica sampling head 63 forms a replica agent filling region 66 inside itself. A sponge 64 coming into contact with the inner surface of the core shroud 34, which is the inspection object, is provided to the distal end of the replica sampling head 63. The replica agent supply pipe 68 communicated to the replica agent filling region 66 is fixed to the replica sampling head 63. The replica agent cartridge 67 is removably attached to the supporting member 20, and removably connected to the replica agent supply pipe 68. The hydraulic cylinder 69 disposed above the replica agent cartridge 67 is attached to the supporting member 20.

Figure 14:
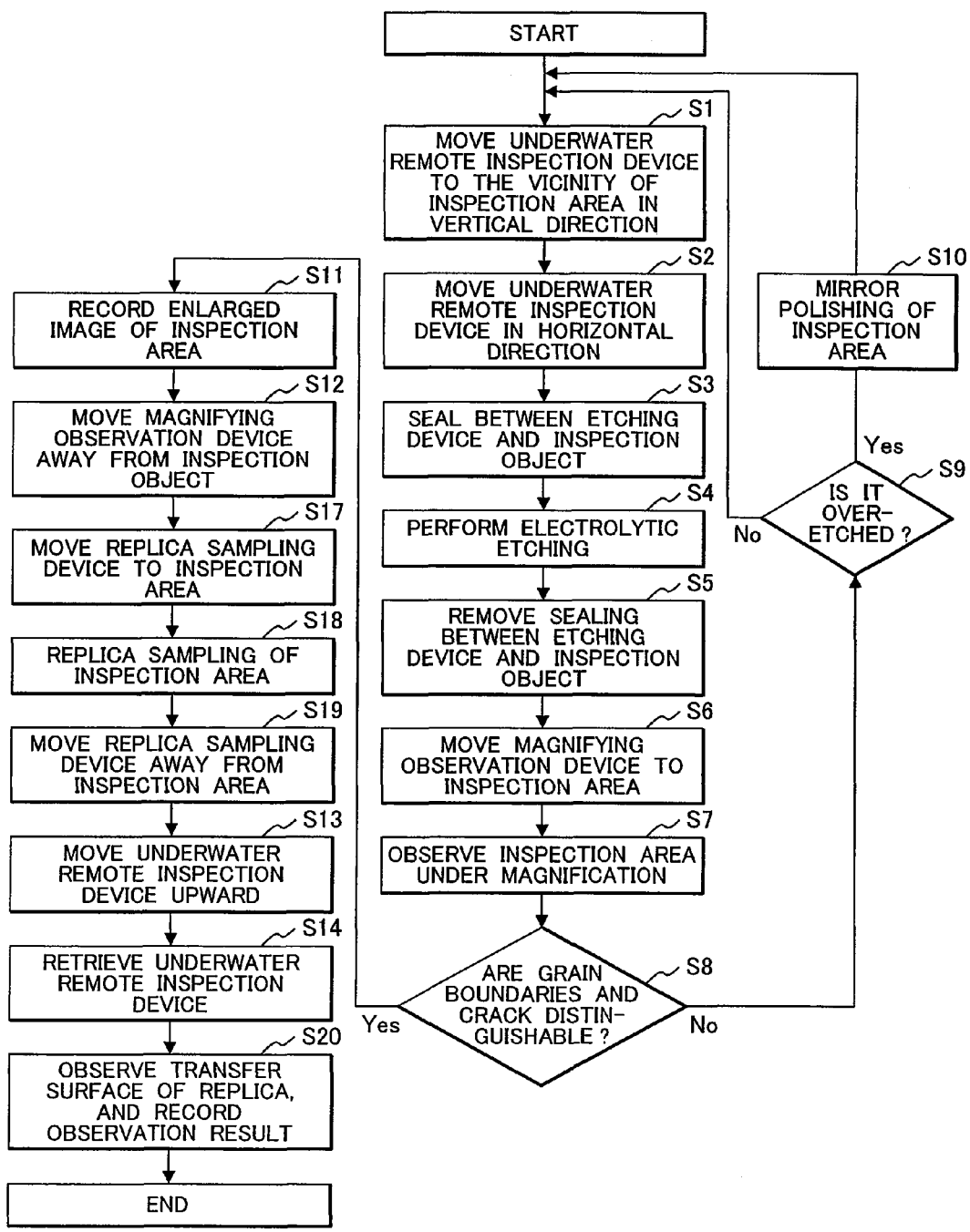
FIG. 14 is a flowchart showing processes of an underwater remote inspection method in embodiment 4 using an underwater remote inspection device shown in FIG. 13.

In the underwater remote inspection method in the present embodiment, each process shown in FIG. 14 is performed. The processes of the underwater remote inspection method shown in FIG. 14 are the processes of the underwater remote inspection method shown in FIG. 5 performed in embodiment 1 with the addition of each process of steps S17, S18, S19, and S20. The steps S17 to S19 are performed between the steps S12 and S13, and the step S20 is performed after the step S14.

In the underwater remote inspection method in the present embodiment, each process of the steps S1 to S8 is sequentially performed. When the determination in the step S8 is "No", the determination of the step S9 is performed, and when the determination in the step S9 is "No", each process of the steps S1 to S8 is performed. When the determination in the step S9 is "Yes", each process of the steps S10 and S1 to S8 is performed. When the determination in the step S8 is "Yes", each process of the steps S11 and S12 is performed.

After the process of the step S12 is completed, the replica sampling device is moved to the inspection area (step S17). The two motors 31 are driven to turn each motor 31 in the same direction at the same rotating speed to turn the transporting rods 25A and 25B in the same direction at the same rotating speed. The underwater remote inspection device 1B moves downward, moving the replica sampling device 62 down to the position facing the etched inspection area 14 of the core shroud 34, which is the inspection object. Then, the two motors 31 are turned in the opposite directions at the same rotating speed to turn the transporting rods 25A and 25B in the opposite directions from each other at the same rotating speed. This moves the underwater remote inspection device 1B in the horizontal direction, and the annular sponge 64 of the replica sampling device 62 comes into contact with the inner surface of the core shroud 34. The underwater remote inspection device 1B is stopped from being moved in the horizontal direction. The sponge 64 is surrounding the etched inspection area 14.

A replica of the inspection area is sampled (step S18). The hydraulic cylinder 69 is driven to eject the replica agent filled in the replica agent cartridge 67 into the replica agent supply pipe 68. The ejected replica agent passes through the replica agent supply pipe 68 and is supplied to the replica agent filling region 66 surrounded by the replica sampling head 63. This replica agent is accumulated in the replica agent filling region 66 as coming into contact with the inspection area 14, and eventually fills the replica agent filling region 66. Whether the replica agent filling region 66 is completely filled with the replica agent or not can be confirmed based on an image taken by the underwater TV 37, showing if the replica agent is in an air-vent hole 65 formed on the upper end portion of the replica sampling head 63 for communicating with the replica agent filling region 66, opened to the outside of the replica sampling head 63. The sponge 64 coming into contact with the inner surface of the core shroud 34 prevents the replica agent supplied into the replica agent filling region 66 from leaking out of the replica sampling head 63 through the joint between the replica sampling head 63 and the core shroud 34. The replica agent filled in the replica agent filling region 66 cures after a predetermined period of time has passed, and the surface form of the inspection area 14 is transferred to the cured replica agent.

The replica sampling device is moved away from the surface of the inspection object (step S19). In the same manner as the step S12 in embodiment 1, the two motors 31 are driven to turn the transporting rods 25A and 25B in the opposite directions from each other at the same rotating speed. This moves the underwater remote inspection device 1B in the horizontal direction away from the core shroud 34, and the replica sampling device 62 is also moved away from the core shroud 34. Eventually, the underwater remote inspection device 1B is stored in the casing 24 of the underwater scanning device 23.

After the completion of the step S19, each process of the steps S13 and S14 is performed to retrieve the underwater remote inspection device 1B and the underwater scanning device 23 on the operation floor. Then, the transfer surface of the replica is observed and the observation result is recorded (step S20). The replica is removed from the replica sampling device 62 of the retrieved underwater remote inspection device 1B, and the transfer surface (the surface that had come into contact with the inspection area 14) of the replica is enlarged by an optical microscope, etc. for observation. This observation result is loaded into a personal computer and stored in a memory.

Each effect attained in embodiment 1 can also be obtained in the present embodiment. The present embodiment is provided with the replica sampling device 62 so that a replica, to which the surface form of the inspection area 14 is transferred, can be obtained. In addition, the present embodiment is provided with the sealing device 9 and the magnifying observation camera 16 so that the time can be shortened, which is required from the time when the underwater scanning device 23 is supported by the core plate 36 to the time when the retrieval of the underwater remote inspection devices 1B is completed after sampling the replica.

[Embodiment 5]

An underwater remote inspection method in embodiment 5, which is another embodiment of the present invention, will be described with reference to the drawings.

Figure 15:
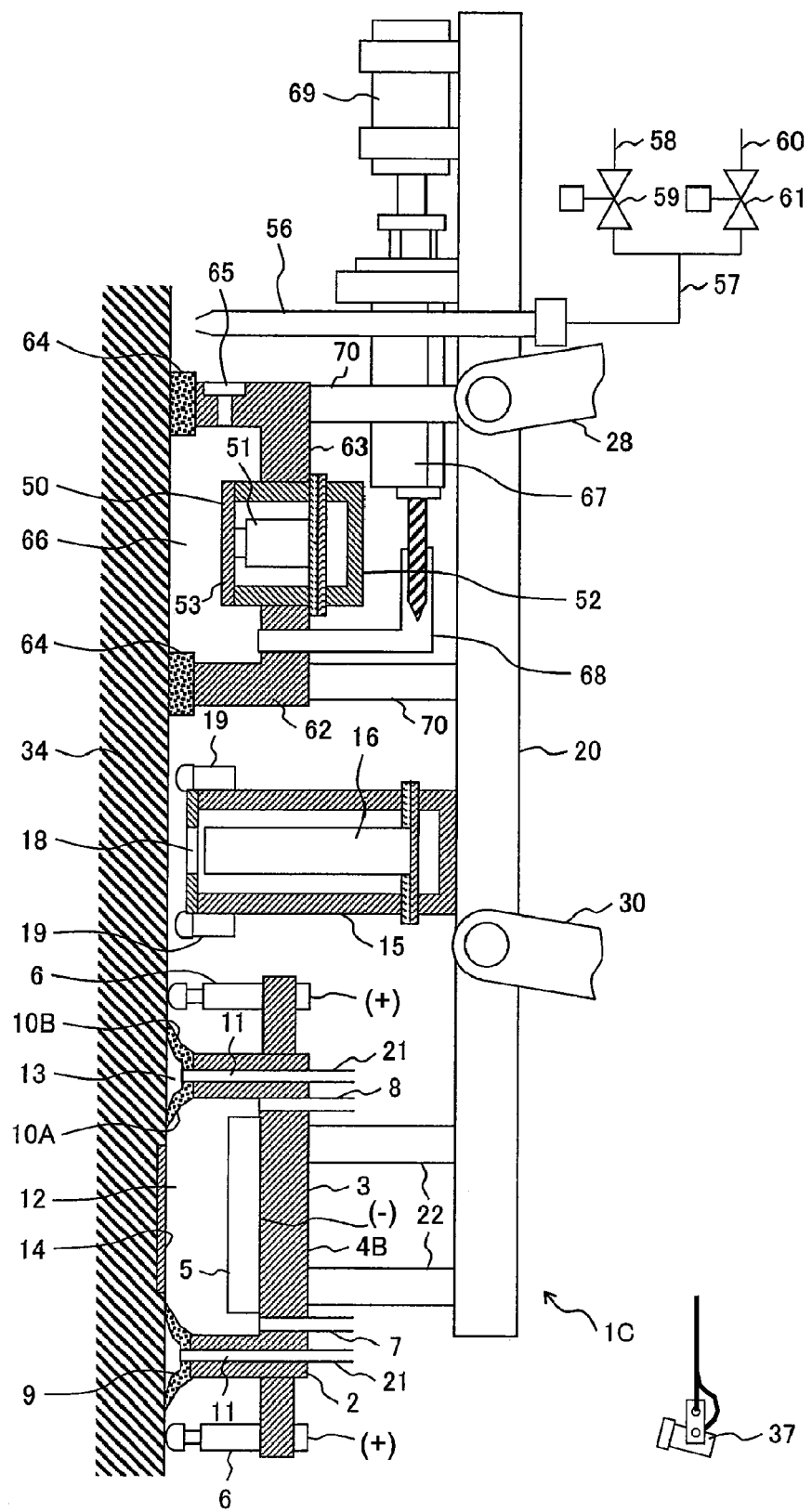
FIG. 15 is a longitudinal sectional view showing an underwater remote inspection device used in an underwater remote inspection method in embodiment 5, which is another embodiment of the present invention.

An underwater remote inspection device 1C (see FIG. 15) used in the present embodiment has a structure in which an ultrasonic cleaning device 50 is added to the underwater remote inspection device 1B used in embodiment 4. This ultrasonic cleaning 50 is provided to the replica sampling head 63, and the distal end portion, which is a part of the ultrasonic cleaning device 50, is disposed in the replica agent filling region 66. The other structures of the underwater remote inspection device 1C are the same as the underwater remote inspection device 1B. The ultrasonic cleaner 50 used in the present embodiment has the same structure as the ultrasonic cleaner 50 used in Embodiment 3.

In the underwater remote inspection method in the present embodiment, each process of the steps S15 and S16 is performed between the steps S5 and S6 in the processes shown in FIG. 14 in the same manner as the processes in embodiment 3 shown in FIG. 12.

Each effect attained in embodiment 4 and the effect attained by the ultrasonic cleaning in embodiment 3 can be obtained in the present embodiment. In the present embodiment, since the ultrasonic cleaning device 50 is installed to the replica sampling head 63, the supporting member 54 provided in embodiment 3 is no longer necessary.

[Embodiment 6]

An underwater remote inspection method in embodiment 6, which is another embodiment of the present invention, will be described with reference to the drawings.

Figure 16:
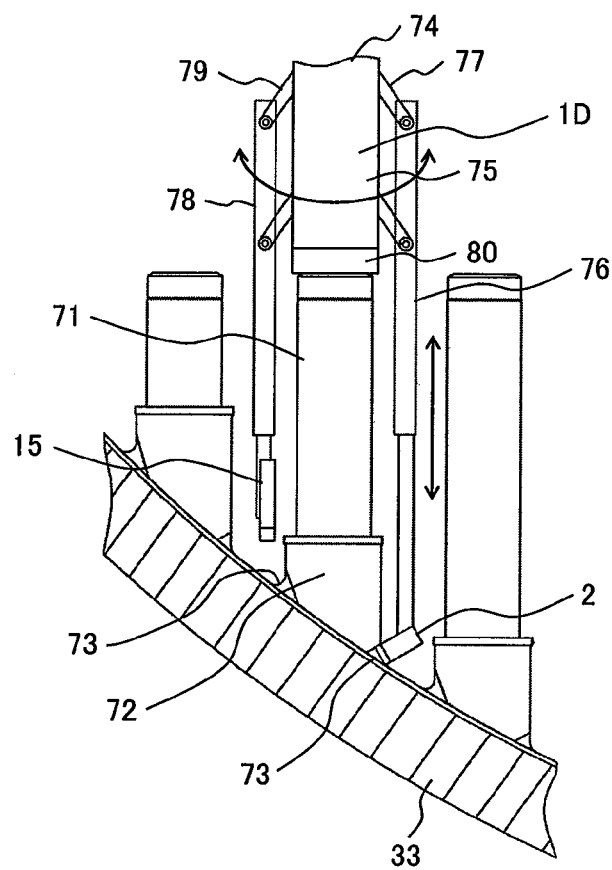
FIG. 16 is an explanatory drawing showing a state in which an underwater remote inspection device is installed to an upper end portion of a control rod drive mechanism housing according to an underwater remote inspection method in embodiment 6, which is another embodiment of the present invention.
Figure 17:
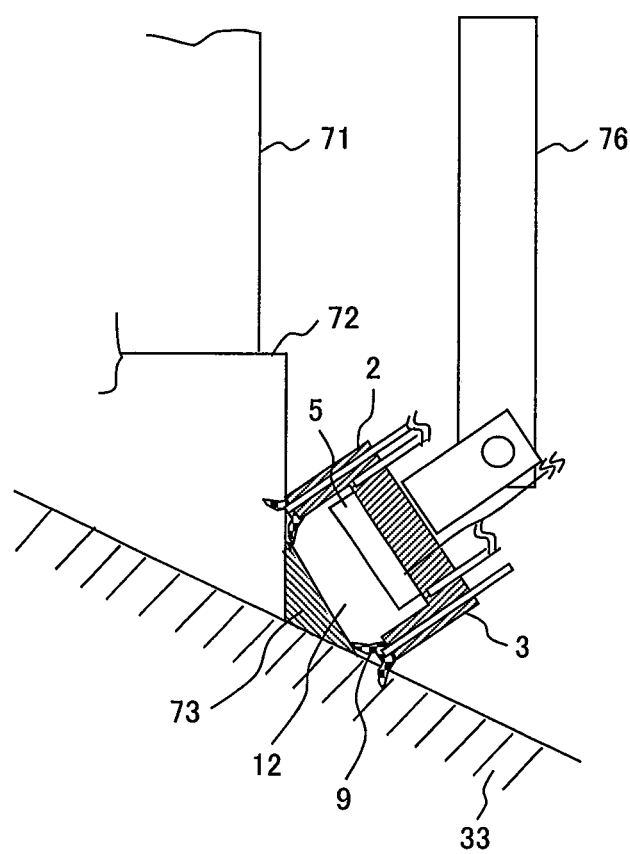
FIG. 17 is an explanatory drawing showing etching of a welding portion of a stub tube, to which the control rod drive mechanism housing is installed, using an etching device of an underwater remote inspection device shown in FIG. 16.

An underwater remote inspection device 1D (see FIGS. 16, 17, and 18) used in the present embodiment is provided with the etching device 2 and the magnifying observation device 15 in the same manner as in the underwater remote inspection device 1. This etching device 2 and the magnifying observation device 15 are the etching device 2 and the magnifying observation device 15 used in embodiment 1. In addition, the underwater remote inspection device 1D is provided with a driving device 74 and arms 76 and 78. The driving device 74 has a casing 75, a rotating device 80 and a lifting/lowering device (now shown). The casing 75 is installed on the rotating device 80. A plurality of links 77 is attached to the lifting/lowering device, and further attached to the arm 76. A plurality of links 79 is attached to the lifting/lowering device and further attached to the arm 78. The lifting/lowering device is installed in the casing 75 to move the links 77 and 78 up and down separately. The etching device 2 is rotatably attached to the lower end portion of the arm 76. The magnifying observation device 15 is rotatably attached to the lower end portion of the arm 78. A side-viewing mirror 81 is provided to the distal end portion of the magnifying observation device 15 (see FIG. 18).

The underwater remote inspection method in the present embodiment using the underwater remote inspection device 1D will be specifically described. The inspection area in the present embodiment is a surface of a welding portion 73 between the reactor pressure vessel 33 and the stub tube 72, to which the CRD housing 71 is fixed (see FIGS. 16 and 17). The underwater remote inspection device 1D is lowered using, for example, a crane provided to a fuel exchange apparatus, and set on an upper end portion of the CRD housing 71 fixed to the stub tube 72 joined by the welding portion 73 which will be the inspection object. To be more specific, the rotating device 80 of the underwater remote inspection device 1D is set on the upper end portion of the CRD housing 71. The arms 76 and 78 are disposed around the mentioned CRD housing 71, and stay between the CRD housing 71 and the other CRD housing 71 adjacent to the CRD housing 71.

The lifting/lowering device is driven to lower the arm 76, and the etching device 2 is moved to the position facing the welding portion 73 of the stub tube 72. The etching device 2 is turned in relation to the arm 76 to set the chamber 3 of the etching device 2 to the predetermined position facing the welding portion 73 (see FIG. 17). The sealing members 10A and 10B of the sealing device 9 come into contact with the bottom portion of the reactor pressure vessel 33, the stub tube 72, and the welding portion 73. The steps S3, S4, and S5 performed in embodiment 1 are also performed in the present embodiment.

Figure 18:
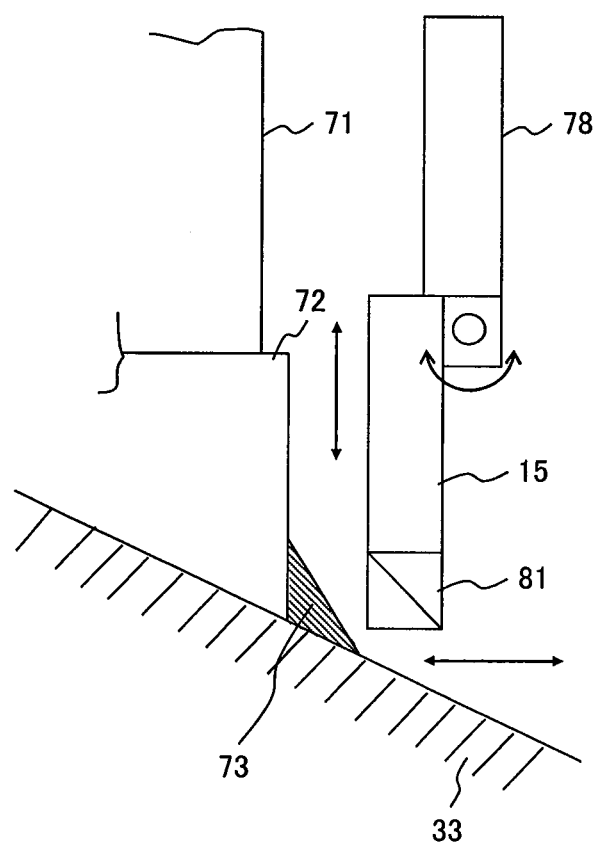
FIG. 18 is an explanatory drawing showing image taking of the welding portion of the stub tube using a magnifying observation device of the underwater remote inspection device shown in FIG. 16.

After the process of the step S5 is completed and etching of the surface of the predetermined portion of the welding portion 73 is completed, the rotating device 80 is rotated to dispose the side-viewing mirror 81 provided to the magnifying observation device 15 in the position facing the etched area in the surface of the welding portion 73 (see FIG. 18). In the present embodiment, each processes of the steps S6 and S7 performed in embodiment 1 is performed. In the step S7, an image of the etched surface of the welding portion 73 is taken by the magnifying observation camera 16.

When the determination in the step S8 after the completion of the step S7 is "No", the determination of the step S9 is performed, and when the determination in the step S9 is "No", each process of the steps S1 to S8 is performed. When the determination in the step S9 is "Yes", each process of the steps S10 and S1 to S8 is performed. When the determination in the step S8 is "Yes", the process of the step S11 is performed. Then, the underwater remote inspection device 1D is removed from the CRD housing 71.

Each effect attained in embodiment 1 can also be obtained in the present embodiment. The etching device 2 of the underwater remote inspection device 1D can be inserted between CRD housings 71, which are narrow portions, allowing inspection in the narrow portion to be performed.

The above-described embodiment 6 is applicable also for inspecting a surface of a structure in a pressurized water reactor. In the pressurized water reactor, a plurality of in-core instrumentation tubes is fixed to the bottom portion of the reactor pressure vessel, penetrating the reactor pressure vessel. After the operation of the pressurized water reactor is shutdown, fuel assemblies and reactor internals in the reactor pressure vessel of the pressurized water reactor are taken out outside. Then, the underwater remote inspection device 1D is carried into the reactor pressure vessel to be installed to the upper end portion of the in-core instrumentation tube in the same manner as in embodiment 6. The etching device 2 and the magnifying observation device 15 are rotated around the in-core instrumentation tube to etch the surface of the welding portion between the in-core instrumentation tube and the inner surface of the reactor pressure vessel in the same manner as in embodiment 6.

[Industrial Applicability]

The present invention can be used for inspection of a surface of a structure in a reactor pressure vessel of a boiling water reactor plant and a pressurized water reactor plant.

[Reference Signs List]

1, 1A, 1B, 1C, 1D: underwater remote inspection device, 2: etching device, 3: chamber, 5: negative electrode, 6: positive electrode, 8: etchant exhaust pipe, 9: sealing device, 10A, 10B: sealing member, 11: suction passage, 12: etchant filling region, 13: sealing region, 14: inspection area, 15: magnifying observation device, 16: magnifying observation camera, 17, 52: waterproof container, 19: LED light, 23, 23A: underwater scanning device, 24, 38, 75: casing, 25A, 25B: transporting rod, 26A, 26B: moving body, 27, 28, 28A, 30: link, 31, 31A, 31B: motor, 33: reactor pressure vessel, 34: core shroud, 39: fixing device, 50: ultrasonic cleaning device, 51: ultrasonic oscillator, 53: ultrasonic diaphragm, 62: replica sampling device, 63: replica sampling head, 66: replica agent filling region, 67: replica agent cartridge, 68: replica agent supply pipe, 71: control rod drive mechanism housing, 74: driving device, 76, 78: arm, 80: rotating device.

What is claimed is:

1. An underwater remote inspection method for a reactor vessel, comprising:
a first step of moving an underwater remote inspection device to a position facing an inspection area of an inspection object underwater, the underwater remote inspection device has an etching device and a magnifying camera device mounted to a supporting member, wherein the etching device has a chamber mounted to the supporting member, electrode members provided to the chamber, and a sealing device provided to a distal end portion of the chamber, facing the surface of the inspection object, and wherein the sealing device has an annular first sealing member attached to the distal end portion of the chamber, an annular second sealing member surrounding the first sealing member, attached to the distal end portion of the chamber, and a pipe line communicated to a sealing region formed between the first and the second sealing members, connected to a suction apparatus for reducing a pressure in the region;
a second step of bringing a distal end portion of each of the first and second sealing members into contact with a surface of the inspection object;
a third step of reducing pressure of the sealing region formed between the first and the second sealing members;
a fourth step of supplying an agent for etching to an etchant filling region formed in the chamber;
a fifth step of etching the inspection area surrounded by the sealing device by applying power to the electrode members while the agent is present in the etchant filling region;
a sixth step of discharging the agent for etching from the etchant filling region by supplying pure water to the etchant filling region;
a seventh step of releasing a pressing force of the first and second sealing members by increasing pressure in the sealing region formed between the first and second sealing members after the agent for etching is discharged from the etchant filling region;
an eighth step of moving the magnifying camera device to a position facing the inspection area by moving the underwater remote inspection device after the seventh step;
a ninth step of taking an image of the inspection area by the magnifying camera device;
a tenth step of determining whether it is possible to distinguish a crack from grain boundaries of metal structure of the inspection area by using the image of the inspection area obtained by the magnifying camera device;
an eleventh step of storing the image of the inspection area in a memory device when the crack is distinguished from the grain boundaries of the metal structure; and
a twelfth step of determining whether the inspection area is sufficiently etched by using the image of the inspection area when the crack cannot be distinguished from the grain boundaries;
wherein when it is determined that the inspection area is not sufficiently etched, the steps from the first step to the twelfth step are repeated.

2. The underwater remote inspection method according to claim 1, further comprising the steps of:
covering the etched inspection area with a replica sampling head;
injecting a replica agent into a replica agent filling region formed by covering the etched inspection area with the replica sampling head; and
retrieving a replica from the replica sampling head, the replica including a transfer of a surface form of the surface structure of the material of the inspection area.

3. The underwater remote inspection method according to claim 1, further comprising the step of:
ultrasonically cleaning the etched inspection area.

4. The underwater remote inspection method according to claim 3, further comprising the step of:
covering the ultrasonically cleaned inspection area with a replica sampling head;
injecting a replica agent into a replica agent filling region formed by covering the ultrasonically cleaned inspection area with the replica sampling head; and
retrieving a replica from the replica sampling head, the replica including a transfer of a surface form of the surface structure of the material of the inspection area.

* * * * *